US010265540B2

(12) United States Patent
Yehezkel

(10) Patent No.: US 10,265,540 B2
(45) Date of Patent: Apr. 23, 2019

(54) MOBILE DEVICE CASE WITH ULTRAVIOLET LIGHT SANITIZER AND LIGHT THERAPY

(71) Applicant: ETS TECHNOLOGIES, LLC, Irvine, CA (US)

(72) Inventor: Shaul Yehezkel, Irvine, CA (US)

( * ) Notice: Subject to any disclaimer, the term of this patent is extended or adjusted under 35 U.S.C. 154(b) by 0 days.

(21) Appl. No.: 15/893,444

(22) Filed: Feb. 9, 2018

(65) Prior Publication Data
US 2018/0161594 A1 Jun. 14, 2018

Related U.S. Application Data

(63) Continuation of application No. 15/266,429, filed on Sep. 15, 2016, now Pat. No. 9,925,390, which is a (Continued)

(51) Int. Cl.
*A61N 5/06* (2006.01)
*H04B 1/3888* (2015.01)
(Continued)

(52) U.S. Cl.
CPC .............. *A61N 5/0624* (2013.01); *A61L 2/10* (2013.01); *A61L 2/26* (2013.01); *A61N 5/0616* (2013.01); *A61N 5/0618* (2013.01); *H04B 1/3888* (2013.01); *H04M 1/17* (2013.01); *H04M 1/185* (2013.01); *H04M 1/21* (2013.01); *A61L 2202/11* (2013.01); *A61L 2202/14* (2013.01); *A61L 2202/16* (2013.01); *A61N 2005/0626* (2013.01); *A61N 2005/0642* (2013.01); *A61N 2005/0644* (2013.01); *A61N 2005/0652* (2013.01);
(Continued)

(58) Field of Classification Search
CPC . A61N 5/0624; A61L 2/00; A61L 2/08; A61L 2/10
USPC .................................................... 250/455.11
See application file for complete search history.

(56) References Cited

U.S. PATENT DOCUMENTS 5,920,075 A 7/1999 Whitehead
6,953,940 B2 10/2005 Leighley et al.
(Continued)

OTHER PUBLICATIONS

International Searching Authority, Written opinion of the international searching authority, PCT/US2016/051785, dated Mar. 23, 2017, 9 pages.
(Continued)

*Primary Examiner* — Jason L McCormack
(74) *Attorney, Agent, or Firm* — Rimas T. Lukas

(57) ABSTRACT

A protective case for a mobile electronic device is provided. The case includes at least one light emitting diode that emits electromagnetic radiation in the range of UV-C light for sanitizing contaminated surfaces. The case also includes additional LEDs that emit light at wavelengths known to have a therapeutic effect such as a blue light for treating seasonal affective disorder. The LEDs are provided in a separate encasement that is detachable from the protective cover configured to receive and protect the mobile electronic device. A short-range wireless receiver is included to communicate with an application installed on the mobile electronic device for controlling the activation, intensity, duration and mode of the LEDs including predetermined treatment or sanitization protocols.

19 Claims, 18 Drawing Sheets

Related U.S. Application Data continuation of application No. PCT/US2016/051785, filed on Sep. 14, 2016.

(60) Provisional application No. 62/219,768, filed on Sep. 17, 2015.

(51) Int. Cl.

| | | |
|---|---|---|
| *H04M 1/17* | (2006.01) | |
| *H04M 1/21* | (2006.01) | |
| *A61L 2/10* | (2006.01) | |
| *A61L 2/26* | (2006.01) | |
| *H04M 1/18* | (2006.01) | |

(52) U.S. Cl.
CPC .......... *A61N 2005/0659* (2013.01); *A61N 2005/0661* (2013.01); *A61N 2005/0662* (2013.01); *A61N 2005/0663* (2013.01)

(56) References Cited

U.S. PATENT DOCUMENTS

| | | |
|---|---|---|
| 7,424,314 B2 | 9/2008 | Park |
| 8,481,970 B2 | 7/2013 | Cooper et al. |
| 9,006,680 B2 | 4/2015 | Bettles et al. |
| 9,114,183 B2 | 8/2015 | Campagna |
| 9,925,390 B2 * | 3/2018 | Yehezkel ............ A61N 5/0624 |
| 2006/0183516 A1 | 8/2006 | Ham |
| 2008/0255498 A1 * | 10/2008 | Houle .................. A61C 17/02 604/20 |
| 2009/0142626 A1 | 6/2009 | Orita et al. |
| 2010/0121156 A1 * | 5/2010 | Yoo ..................... G06F 19/3418 600/300 |
| 2011/0077061 A1 * | 3/2011 | Danze .................. H04M 1/185 455/575.1 |
| 2013/0201653 A1 * | 8/2013 | Shoemake ............ G03B 15/02 362/3 |
| 2014/0001374 A1 * | 1/2014 | Ullman ................... A61L 2/088 250/428 |
| 2015/0180527 A1 * | 6/2015 | Fathollahi ............ H04B 1/3888 455/575.8 |
| 2015/0215439 A1 * | 7/2015 | Stanimirovic ........ H04M 1/215 455/572 |
| 2015/0231408 A1 | 8/2015 | Williams et al. |
| 2016/0036952 A1 * | 2/2016 | Kim ......................... A61L 2/10 455/575.8 |
| 2016/0086458 A1 * | 3/2016 | Biggs ....................... G08B 6/00 381/151 |
| 2016/0089457 A1 | 3/2016 | Liao et al. |
| 2016/0089458 A1 | 3/2016 | Liao et al. |
| 2016/0106872 A1 * | 4/2016 | Martinez .................. A61L 2/10 250/492.1 |
| 2016/0129279 A1 * | 5/2016 | Ferolito ............... A61N 5/0618 607/89 |
| 2016/0234356 A1 * | 8/2016 | Thomas ............... H05K 9/0069 |

OTHER PUBLICATIONS

International Searching Authority, International search report, PCT/US2016/051785, dated Mar. 23, 2017, 6 pages.

* cited by examiner

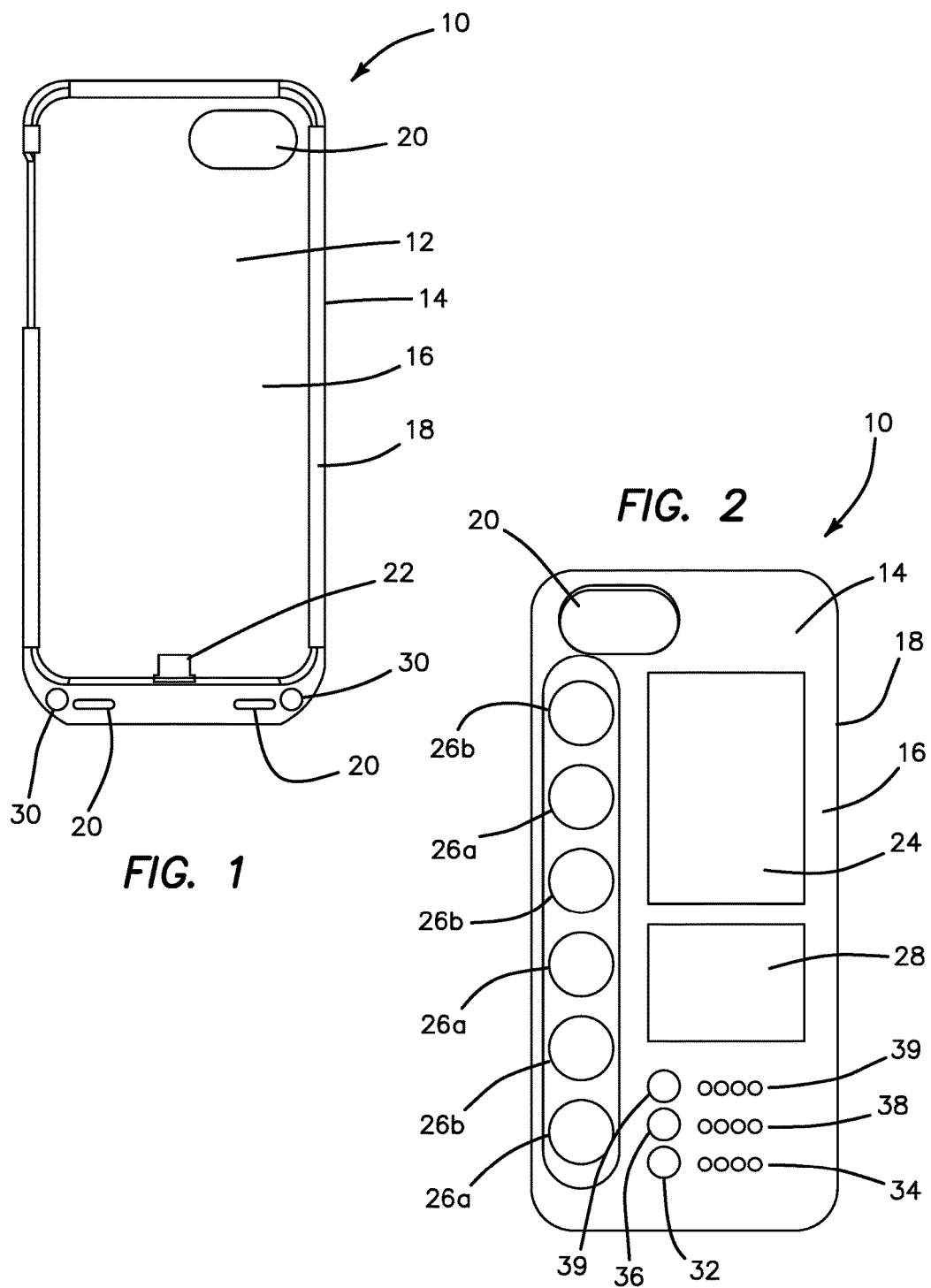

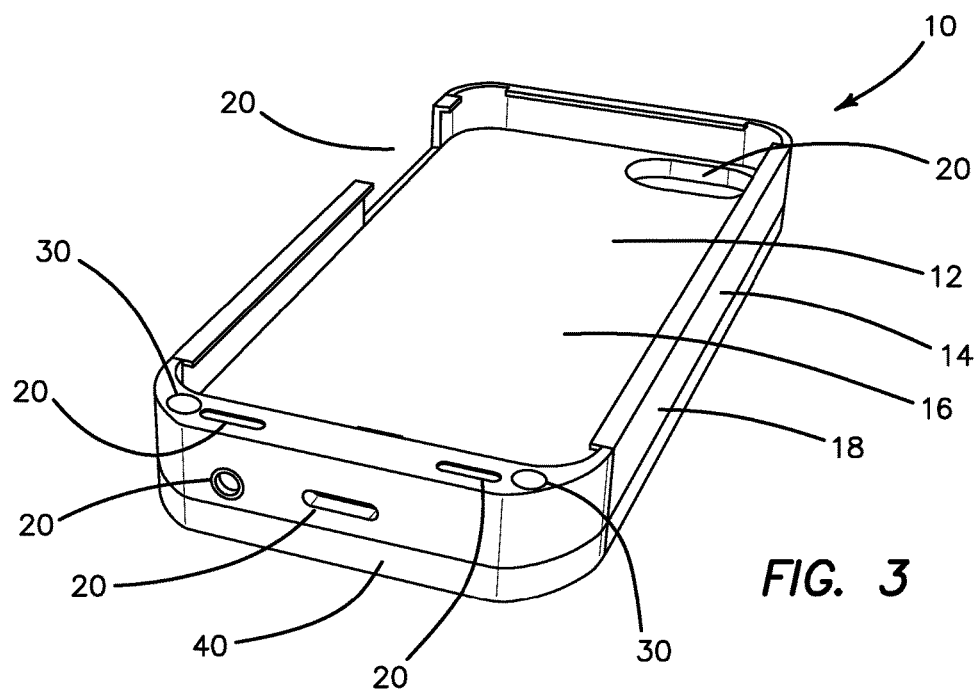
FIG. 3
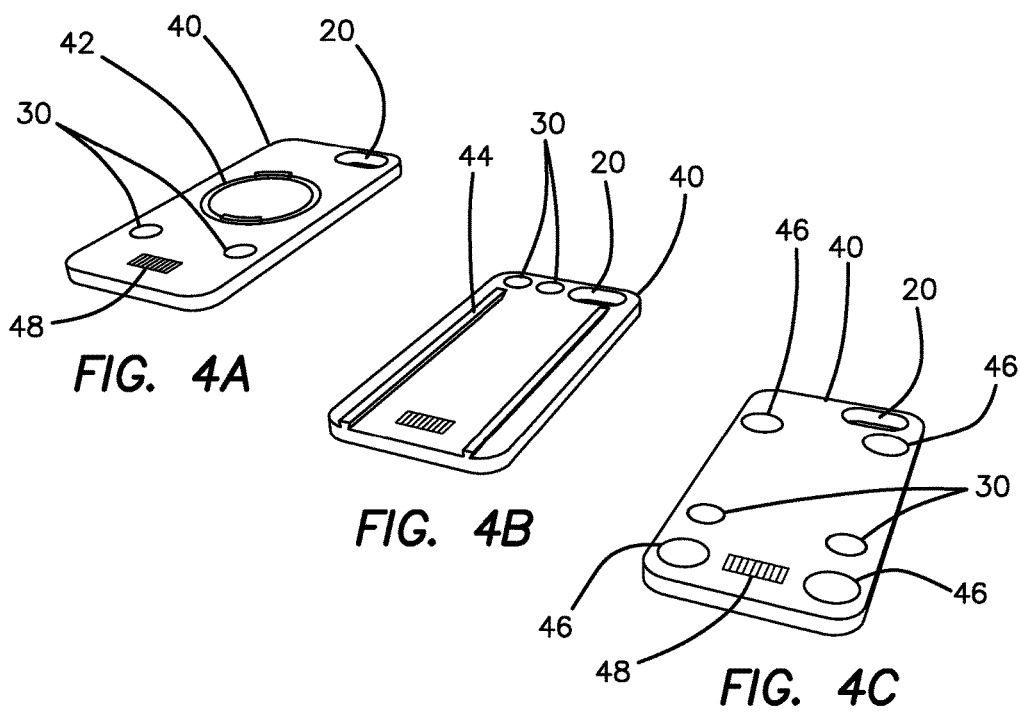
FIG. 4A
FIG. 4B
FIG. 4C

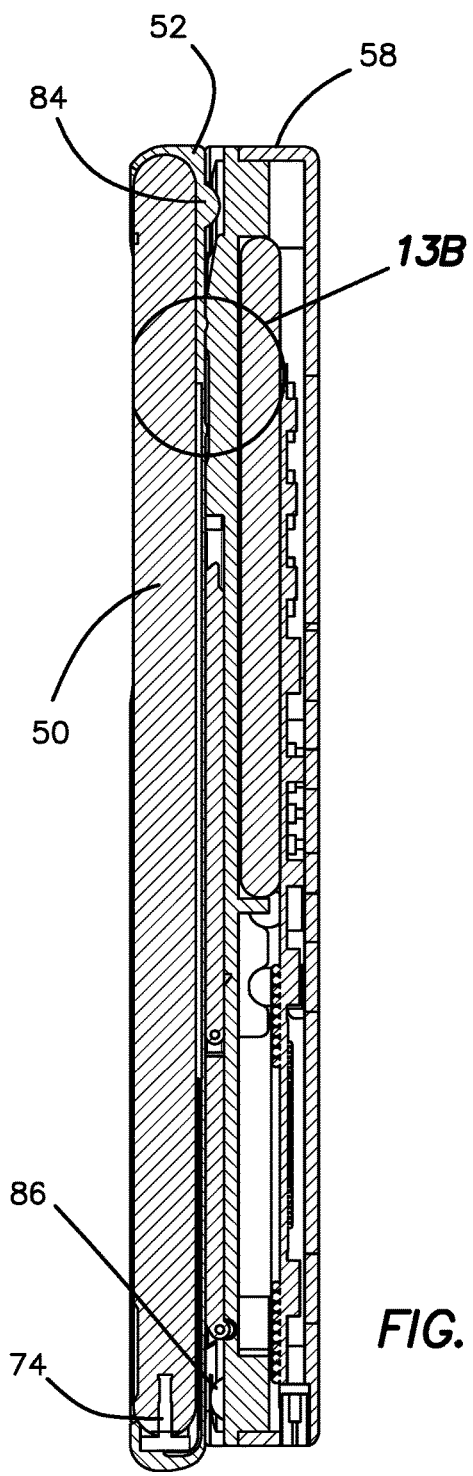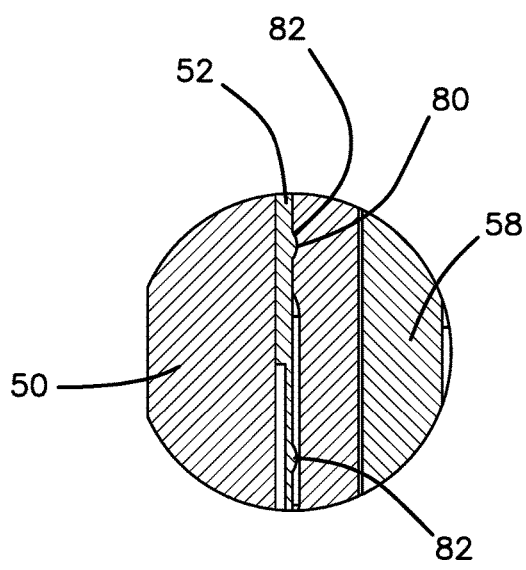
FIG. 13A
FIG. 13B

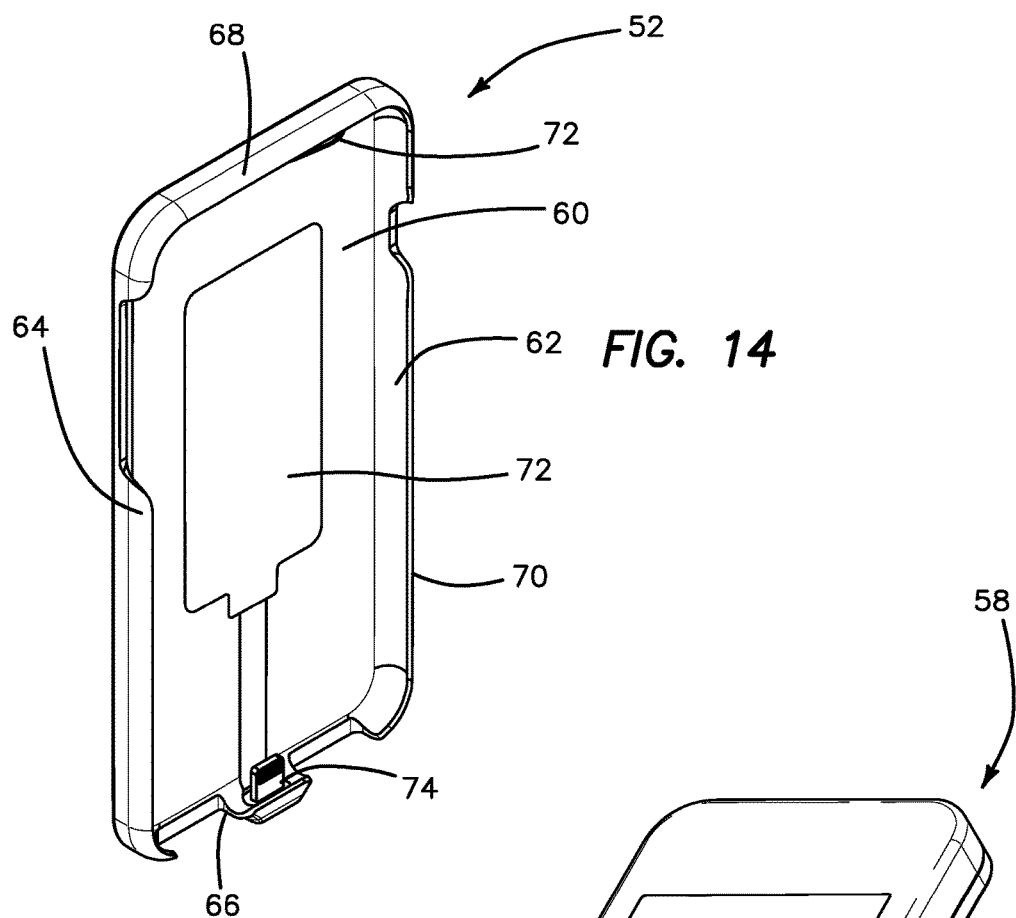
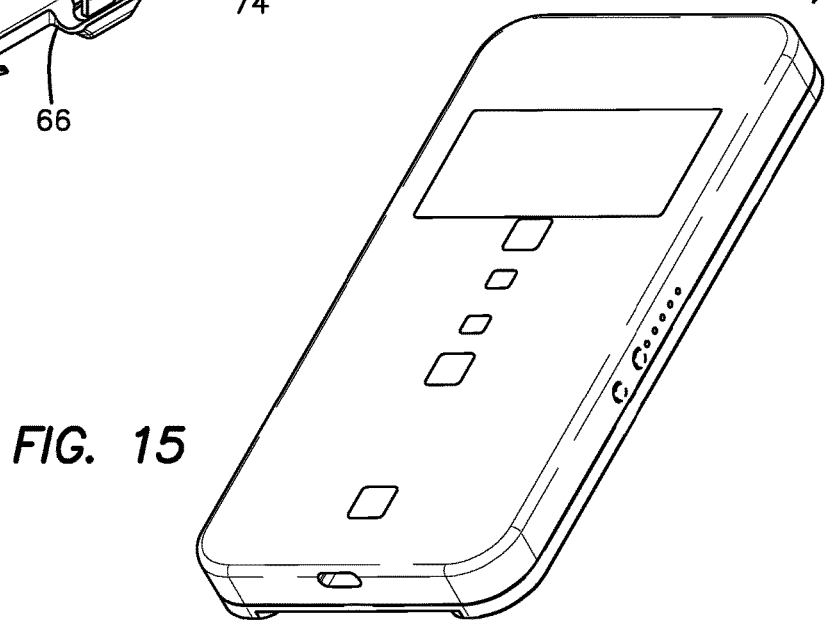

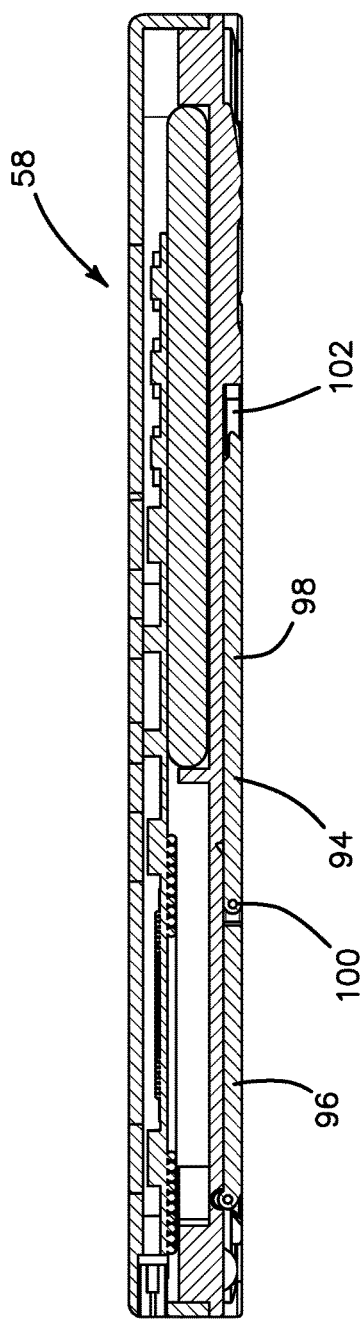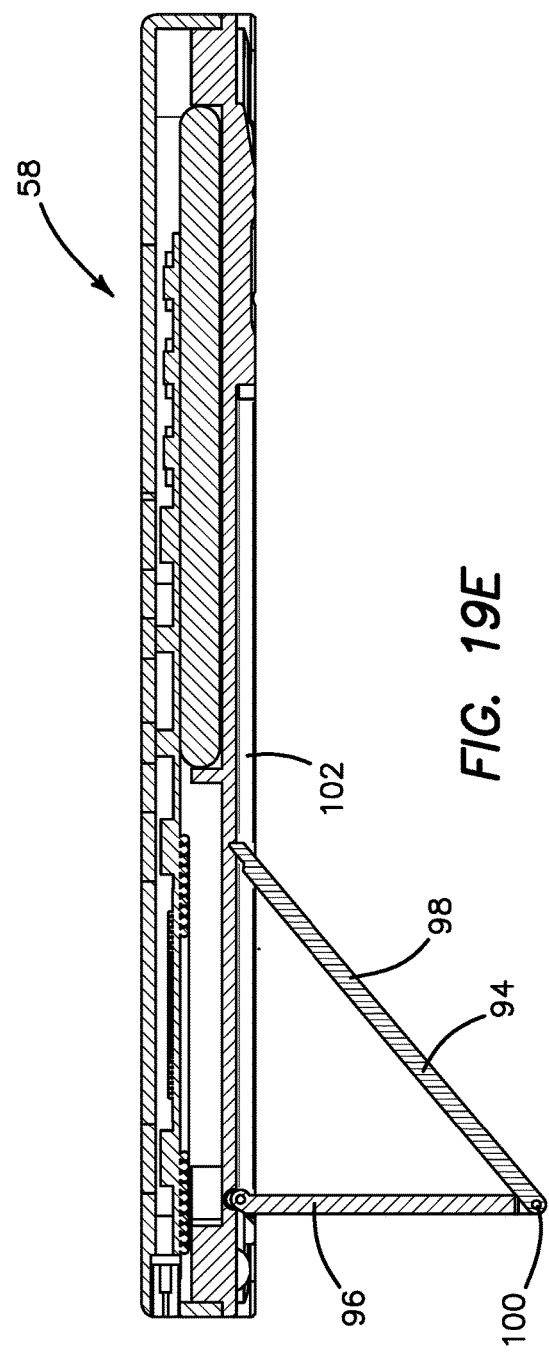

MOBILE DEVICE CASE WITH ULTRAVIOLET LIGHT SANITIZER AND LIGHT THERAPY

CROSS-REFERENCE TO RELATED APPLICATIONS

This application is a continuation application of U.S. patent application Ser. No. 15/266,429 filed on Sep. 15, 2016 entitled "Mobile device case with ultraviolet light sanitizer and light therapy" incorporated by reference in its entirety which claims priority to and benefit of U.S. Provisional Patent Application No. 62/219,768 filed on Sep. 17, 2015 entitled "Mobile device case with ultraviolet light sanitizer and light therapy" incorporated herein by reference in its entirety and is a continuation of International Application No. PCT/US2016/051785 entitled "Mobile device case with ultraviolet light sanitizer and light therapy" filed on Sep. 14, 2016 incorporated herein by reference in its entirety which claims priority to and benefit of U.S. Provisional Patent Application No. 62/219,768 filed on Sep. 17, 2015 entitled "Mobile device case with ultraviolet light sanitizer and light therapy" incorporated herein by reference in its entirety.

FIELD OF THE INVENTION

This application is generally related to portable light treatment devices, and in particular, to cases for protecting hand-held mobile communication devices such as cellular/smart phones. The case having one or more radiation emitters including but not limited to ultraviolet (UV) light emitters configured for personal, hand-held-ready disinfecting, sanitizing and germicidal purposes and/or blue light emitters for portable light therapy treatments.

BACKGROUND OF THE INVENTION

It is well established that ultraviolet (UV) radiation is effective in killing microorganisms including but not limited to surface bacteria, viruses, yeasts, molds, dust mites and flea eggs. UV radiation is used widely for sanitizing and disinfecting surfaces in various industries including healthcare (hospital, wound disinfection and healing), food processing, research laboratories, air purification systems and water purification applications. Ultraviolet radiation/light is electromagnetic radiation having a wavelength ranging from approximately ten nanometers (nm) to approximately four hundred nanometers. Ultraviolet-C (UV-C) is a range of electromagnetic radiation having a wavelength ranging from approximately one hundred nanometers to approximately two hundred eighty nanometers. Ultraviolet-B (UV-B) is electromagnetic radiation having a wavelength ranging from approximately two hundred eighty to approximately three hundred fifteen nanometers and ultraviolet-A (UV-A) is electromagnetic radiation having a wavelength ranging from approximately three hundred fifteen to approximately four hundred nanometers. UV-C light in particular has demonstrated to be up to 99.9% effective in the sanitization of microorganisms and biological pollutants/pathogens such as viruses, bacteria, mold dust mites and flea eggs. UV-C light induces changes in the structure of DNA leading to the production and accumulation of cyclobutane pyrimidine dimers (CPDs), in turn distorting the DNA molecule, causing cellular damage.

Recently, blue light has been receiving more attention and has been shown to have an intrinsic antimicrobial effect without the addition of exogenous photosensitizers. Blue light is also much less detrimental to mammalian cells compared to UV light. Blue light is electromagnetic radiation in the range of approximately four hundred and five nanometers to approximately four hundred seventy nanometers. Furthermore, blue light has been shown to effectively treat seasonal affective disorder (SAD) and new indications have been studied with positive results in the use of blue light for non-seasonal depression, bulimia, sleep disorders and non-seasonal circadian disorders such as jet lag.

Public awareness has increased not only of germs as the causes of diseases, but also of the ways in which germs are spread. In the last few years, the world has been witness to at least one flu pandemic, the rise of multiple and even fully antibiotic resistant bacteria including antibiotic-resistant sexually transmitted diseases, the spread of norovirus, the threat of Middle East Respiratory Syndrome (MERS), Ebola and Zika. Also, research is revealing the association of germs with a number of diseases including obesity, neurological disorders and mental health. Therefore, there is a need to take precautions against pathogens and purify the environment. Whereas most everyone nowadays carries a portable mobile communication device, many do not carry sanitizing gels and disinfectant wipes. Furthermore, one may be reluctant to carry bulky wipes and bottles of disinfectant on one's person; whereas, most everyone carries a cell phone. Also, there are some concerns with chronic, widespread use of sanitizing gels because of the risk of antibiotic resistance, alcohol poisoning, hormone disruption, weakened immune system and toxic chemical ingredients. The present invention advantageously combines well-known light treatment modalities with the ubiquitous mobile communication devices in the form a cell phone case to empower users to protect against germs in a quick, easy and portable manner when on the go. The present invention can be used to conveniently sterilize pathogenic microorganisms from personal contact items such as telephone receivers, key pads, computer keyboard and computer pointer devices, automated teller machine (ATM) touch screens, desk tops, counter tops, automotive surfaces, airplane surfaces, public transportation surfaces, theater surfaces, restaurant surfaces, cutting boards, kitchen utensils, keys, eye glasses, other personal items, toilet seats and flush handles, sinks faucet handles and knobs, children's toys and gym equipment.

SUMMARY OF THE INVENTION

According to one aspect of the invention, an accessory for use with a mobile electronic device is provided. The accessory includes a casing defining a cavity and configured to be removably connectable to a mobile electronic device. At least one light source connected to the casing and configured to emit electromagnetic radiation in the range of ultraviolet light is provided. A power source connected to the casing and configured to power the at least one light source and at least one controller is configured to control the activation of the at least one light source.

According to another aspect of the invention, an accessory for use with a mobile electronic device is provided. The accessory includes a casing defining an internal cavity and configured to be removably connectable to a mobile electronic device. At least one light source connected to the casing and configured to emit electromagnetic radiation that is therapeutic for a human and having a wavelength in the range of approximately 400-1000 nanometers. A power source connected to the casing and configured to power the at least one light source and at least one controller is configured to control the activation of the at least one light source.

According to another aspect of the invention, an accessory for use with a mobile electronic device is provided. The accessory includes a first case portion configured to protect the mobile electronic device. The first case portion including a back wall configured to extend across at least a portion of the mobile electronic device, a right side wall configured to extend along at least a portion of a right side of the mobile electronic device, a left side wall configured to extend along at least a portion of the left side of the mobile electronic device, a bottom wall configured to extend along at least a portion of a bottom of the mobile electronic device, a top wall configured to extend along at least a portion of a top of the mobile electronic device, and a front opening configured such that a display of the mobile electronic device is visible through the front opening. The accessory includes a second case portion connected to the first case portion. The second case portion includes at least one source of ultraviolet radiation configured for sanitizing or sterilizing a surface external to the case.

An accessory for use with a mobile electronic device is provided. The accessory includes a first case portion configured to protect the mobile electronic device. The first case portion includes a back wall configured to extend across at least a portion of the mobile electronic device. The back wall has an opening adapted to expose a camera of the mobile electronic device. The first case portion further includes a right side wall configured to extend along at least a portion of a right side of the mobile electronic device, a left side wall configured to extend along at least a portion of the left side of the mobile electronic device, a bottom wall configured to extend along at least a portion of a bottom of the mobile electronic device, a top wall configured to extend along at least a portion of a top of the mobile electronic device, and a front opening configured such that a display of the mobile electronic device is visible through the front opening. The accessory includes a second case portion connected to the first case portion such that the second case portion is movable between a first position in which the opening that is adapted to expose a camera of the mobile electronic device is not covered by the second case portion and a second position in which an outer perimeter of the second case portion is in substantial alignment with an outer perimeter of the first case portion and covers the opening that is adapted to expose a camera of the mobile electronic device. The second case portion including at least one ultraviolet radiation source configured for emitting ultraviolet radiation away from the second case portion for sanitizing or sterilizing a surface external to the case.

BRIEF DESCRIPTION OF THE DRAWINGS

FIG. 1 is a top view of a case according to the present invention.

FIG. 2 is a bottom view of a case according to the present invention.

FIG. 3 is a top perspective view of a case and detachable unit according to the present invention.

FIG. 4A is a bottom perspective view of a detachable unit according to the present invention.

FIG. 4B is a bottom perspective view of a detachable unit according to the present invention.

FIG. 4C is a bottom perspective view of a detachable unit according to the present invention.

FIG. 13A is a cross-sectional view taken along line 13-13 of FIG. 10 according to the present invention.

FIG. 13B is a sectional view of detail 13B of FIG. 13A according to the present invention.

FIG. 14 is a top perspective view of a case without a detachable unit according to the present invention.

FIG. 15 is a bottom perspective view of a detachable unit according to the present invention.

FIG. 19D is a cross-sectional view taken along line 19D-19D of FIG. 19B according to the present invention.

FIG. 19E is a cross-sectional view taken along line 19E-19E of FIG. 19C according to the present invention.

DETAILED DESCRIPTION OF THE INVENTION

Figure 5:
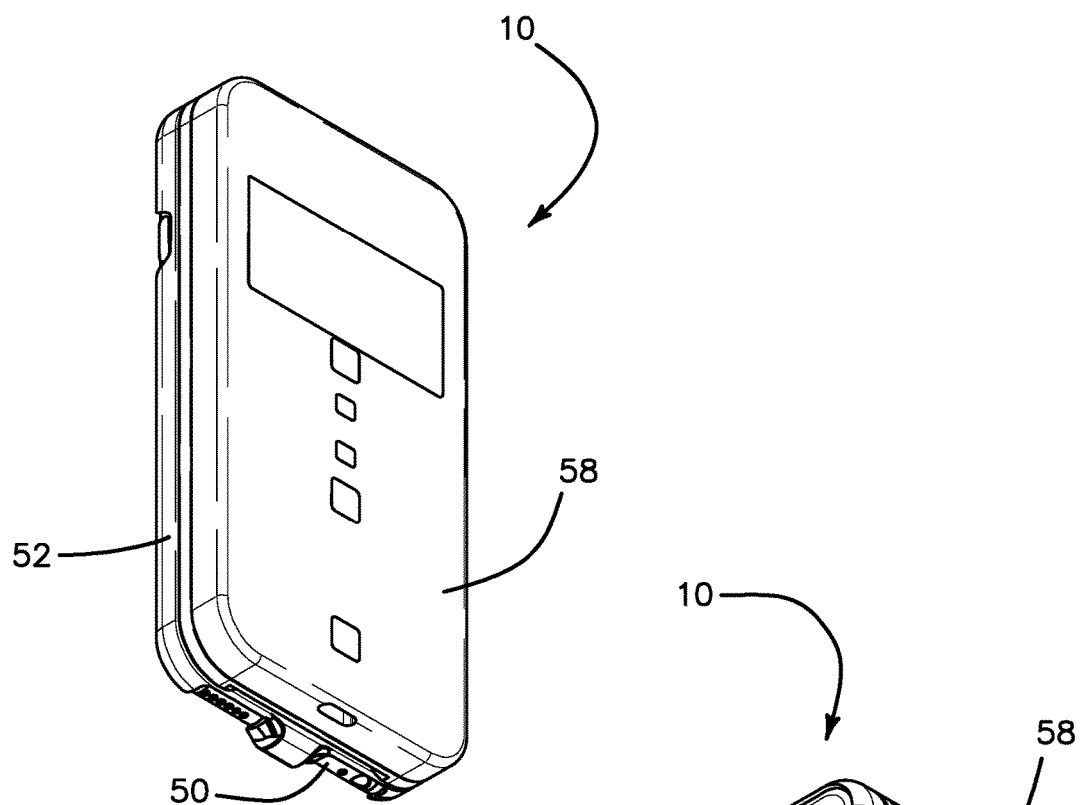
FIG. 5 is a bottom perspective view of a case connected to a mobile device according to the present invention.
Figure 6:
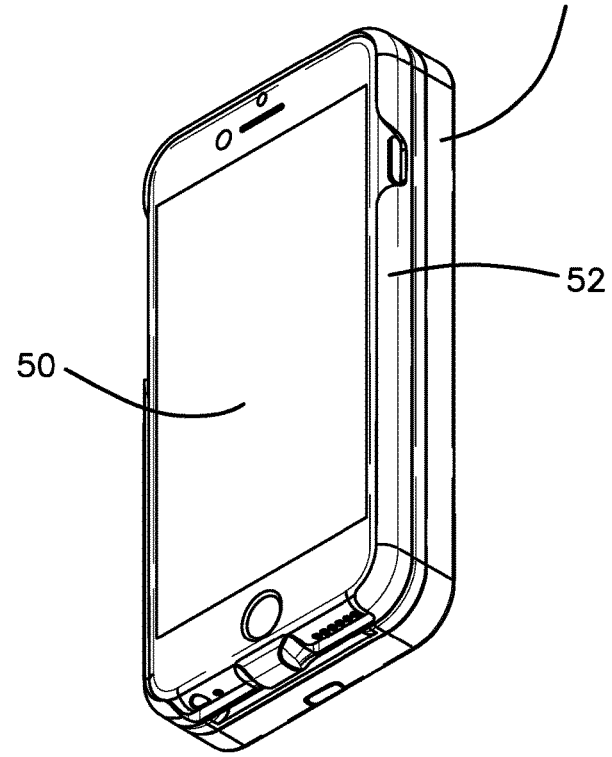
FIG. 6 is a top perspective view of a case connected to a mobile device according to the present invention.

Turning now to FIGS. 1 and 2, there is shown a case 10 according to the present invention. The case 10 is sized and configured to connect to a mobile device such as a cellular phone. Different sizes, shapes and configurations of the case 10 are provided to conform to any type of mobile device and manufacturer and is not limited to cellular and smart phones but may be sized and configured for any device such as a portable tablet, personal digital assistant, portable computer, any electronic device and the like. The case 10 is adapted to protect the mobile device from impact, damage, scratches, et cetera using materials and constructions well known in the art such as rubber, plastic, polymer, metal and the like designed to protect edges, visual displays and built-in cameras while providing access to audio inputs/outputs, visual displays, control switches and the like.

Generally, the case 10 includes an inner surface 12 and an outer surface 14 defining a thickness therebetween. The case 10 has a backside base 16 that is generally rectangular in shape to correspond to the shape of the mobile device. A sidewall 18 is generally integrally formed with the base 16 and surrounds the perimeter of the base 16 to create a safe container for receiving the mobile device against the inner surface 12. The base 16 and sidewall 18 include a variety of apertures 20 for accessing volume controls, on/off buttons, image collectors such as cameras, touchscreen electronic visual displays, audio output speakers and audio input microphones and the like. The case 10 may optionally include an internal interface connector 22 to electronically interface with the mobile device itself. For example, the case 10 may include a male member configured to connect electronically with a female member on the mobile device. Such connectors and interfaces are well known and include but are not limited to various pin connectors such as the LIGHTENING connector by APPLE computer and standard universal serial bus (USB) plugs for carrying a digital signal between the case 10 and the mobile device (not shown). The internal interface connector 22 couples with the existing interface on the mobile device to charge the internal power source of the mobile device and permit use of the various interfaces and operating systems while engaged such as the connector power button, volume control, etc. The mobile device is securely inserted into the case 10 and connected therewith such as by a friction or interference fit, tongue-and-groove insertion of the mobile device into the case 10 or other engagement means well known in the art. If an interface connector 22 is employed, connection of the case 10 to the mobile device results in the alignment of the connector 22 with the mobile device such that the connector 22 is successfully mated with the mobile device while connected and inside the case 10. The case 10 as described herein is not intended to be limiting but only exemplary as cases evolve to adapt to the ever-evolving changes in sizes, shapes of electronic devices and protection technologies inherent in portable electronics. The case 10 herein refers to any case and is not limited to the descriptions herein.

With particular reference to FIG. 2, the case 10 includes at least one UV light 26A configured to emit ultraviolet radiation. In one variation, the UV light is selected to emit ultraviolet radiation in any wavelength range effective for killing various microbes, and sanitization and disinfection of various surfaces as described above. In another variation, the UV light 26A is selected to emit ultraviolet radiation in the UV-C range. Preferably, the UV light source is a light-emitting diode (LED) and the case 10 includes at least one UV light-emitting diode (LED) which emits UV light. The UV LED 26A is selected to emit radiation in a frequency range effective for killing various microorganisms, preferably in the UV-C range when activated. As the photosensitivity of microorganisms approximately matches the absorption spectrum of DNA, with a peak at about 260 nm, UV LEDs 26A emitting at approximately 250-270 nm are particularly suitable for disinfection and sterilization. UV-A LEDs (approximately 365 nm) are also known to be effective disinfection and sterilization devices and can also be useful for other applications such as to detect counterfeit currencies. Some examples of semiconductors in UV LEDs include boron nitride, aluminum nitride, aluminum gallium nitride, aluminum gallium indium nitride and diamond. In one variation, the case 10 only includes UV LEDs. In another variation, the case 10 includes only LEDs 26B configured to emit blue light for light therapy purposes described above. In another variation, the case 10 includes a combination of UV LEDs 26A and blue light LEDs 26B as shown in FIG. 2. Of course, the case 10 may include only one type of LED or non-LED light or one or more different types of LEDs or non-LEDs on the same case with separate actuation buttons. Some examples of semiconductors in bright blue LEDs 26B are gallium nitride, indium gallium nitride, silicon carbide and silicon. Blue light has a wavelength range of approximately 450-500 nm. Red and green LEDs can be added to blue LEDs to produce the impression of white light. LEDs 26 are advantageously small and make them suitable for portable applications such as the case 10 of the present invention where compactness is important. LEDs 26 also provide a very high brightness with high-efficiency. The LEDs can have any shape and can be arranged in any manner. For example, the LEDs can be arranged in a linear fashion along one side of the case 10 as shown in FIG. 2 or in a rectangular or circular pattern to allow for different surface coverage configurations. In one variation, the LEDs 26 are located anywhere on the outer surface 14 of the case 10 including on one or more of the base 16 and sidewall 18. Preferably, the LEDs 26 are located on the base backside 16 such that the LEDs 26 are located opposite from the visual display of the mobile device. Thereby, the user may view the visual display of the mobile device to monitor the activation and duration of the LEDs while directing the light away from the user. The UV LEDs 26A are configured to disinfect while the blue light LEDs 26B are configured for light therapy. The power output of the LEDs 26 will vary depending on the desired irradiance intensity allowing for a wide range of effectivity.

The case 10 further includes a power source 24, such as a rechargeable lithium-ion battery, configured for supplying power to the one or more LEDs 26. The power source 24 may also be configured to recharge the battery of the mobile device when connected thereto via the interface connector 22. The power source 24 of the case 10 is configured to not only supply power to the LEDs 26, but also, increase the charging capacity via portable charging.

The case 10 further includes electronic circuitry 28 connected to the power source 24 and LEDs and, optionally, further configured to interface with the mobile device to control battery use, battery charging, activation, deactivation, duration, frequency and intensity of the LEDs, and the like. The electronic circuitry includes a digital processing unit with software and memory. The software interface between the mobile device and the case 10 via the interface connector 22 can be in the form of an application, a mobile app downloadable to the mobile device, and/or a web app providing the user with a display and touchscreen buttons for controlling features of the case 10 and monitoring the functionality of the hardware, battery power and LED intensity, activation and variable duration for a particular target surface. The device may also be provided with an automatic shut-off of the LEDs if, for example, the motion detector of the mobile device senses that the unit is turned upwardly in order to avoid accidental illumination of the user's eyes.

The case 10 further includes a LED on/off switch that may optionally further include safety actuation buttons 30. The safety actuation buttons 30, for example, may include two buttons and require the user to depress both buttons simultaneously to turn on the LEDs to avoid accidental activation and depletion of battery power while, for example, in the user's pocket. The safety actuation buttons 30 may also be configured to only permit activation while the LEDs are facing away from the user. The on/off switch and safety actuation buttons may be located anywhere on the case 10 such as on the top surface, sidewalls as well as on the internal side of a version of the case in which the LEDs are removable/separable from the main case unit which will be explained in greater detail below. The UV LED on/off switch 32 may further include a UV LED duration indicator 34. If the case 10 is provided with both UV and blue light LEDs a separate blue light on/off switch 36 and duration indicator 38 are provided. The case 10 includes a battery charge indicator 39 which displays to the user the remaining energy available in the battery.

Turning now to FIGS. 3-4, there is shown another variation of the case 10. The case 10 includes a detachable unit 40. The detachable unit 40 is removable from the case 10 which allows the user to use the LEDs independently of the case 10 and mobile device. When attached to the case 10, the detachable unit 40 is used as one unit with the case 10 as shown in FIG. 3. Also, the detachable unit 40 permits interchangeability with other detachable units 40 having different LEDs for different purposes such as for counterfeit currency detection or other light color therapies. Also, removing the detachable unit 40 creates a slimmer case 10 when the user wishes to take advantage of only the mobile device protection features of the case 10. The detachable unit 40 may also include its own power supply. The detachable unit 40 is configured to attach to the case 10 via a circular tongue and groove mechanism 42 or straight tongue and groove mechanism 44 shown in FIGS. 4A and 4B, respectively. These mechanisms 42, 44 include locking tabs to securely connect the detachable unit 40 to the case 10. Alternatively, a magnetic mechanism 46 may be employed to connect the two together as shown in FIG. 4C. The electrical connection between the case 10 and the detachable unit 40 will be wireless using either inductive charging or surface mounted contacts 48, avoiding the need to disassemble for attachment purposes.

Turning now to FIGS. 5-13, there is shown another variation of a protective case 10 for use with a mobile/portable electronic device 50. The case 10 includes a first case portion 52 connected to a second case portion 58. The first case portion 52 is configured to receive the mobile electronic device 50 and protect it from impact. The second case portion 58 is configured as an accessory to provide one or more of the therapy and sanitization features described above. In one variation, the second case portion 58 is detachable from the first case portion 52 and serves as a detachable unit of the like described above such that the first case portion 52 continues to house and protect the mobile electronic device 50 when the second case portion/detachable unit 58 is removed. Of course, in another variation, the second case portion 58 is not removable from the first case portion 52. In either case, the second case portion 58 may include additional features such as wireless battery charging capabilities for the mobile electronic device and or second case portion among other features.

Turning now to FIG. 14, there is shown a first case portion 52. The first case portion 52 includes a back wall 60 that is configured to extend across at least a portion of the back side of the mobile electronic device 50, a right side wall 62 that is configured to extend along at least a portion of a right side of the mobile electronic device 50, a left side wall 64 that is configured to extend along at least a portion of the left side of the mobile electronic device, a bottom wall 66 that is configured to extend along at least a portion of a bottom of the mobile electronic device; and a top wall 68 that is configured to extend along at least a portion of a top of the mobile electronic device. The first case portion 52 defines a front opening 70 that is configured to removably receive and retain the mobile electronic device such that a display of the mobile electronic device is visible through the front opening 70. The right side, left side, and bottom walls 62, 64, 66 are shown in FIG. 14 to include openings that are formed on the first case portion 52 in locations that correspond to locations of on/off switches, volume controls, speakers, microphones, jacks and the like on a mobile electronic device that provide access without removing the first case portion 52 from the device 50. The back wall 60 also includes an opening 72 that is formed in the location that corresponds to the location of a flash and/or camera aperture on the device 50. The opening 72 for the camera/flash is more clearly visible in FIG. 11. The back wall 60 has a front surface and a back surface. A mobile electronic device 50 is placed against the front surface of the back wall 60. The back, right, left, bottom and top walls 60, 62, 64, 66, 68 fit tightly around the mobile electronic device 50. As mentioned previously, the mobile electronic device 50 can be any electronic device such as a mobile phone. In the variation in which a mobile phone is the electronic device, the first case portion 52 is shaped to conform to the external shape of the mobile phone without significantly affecting the size and usability of the mobile phone. The first case portion 52 is configured to protect/shield the mobile electronic device 50 and, as such, is made of suitable protective material such as rubber, plastic and the like known in the art to prevent damage to the device 50. The first case portion 52 serves as a casing defining a cavity that conforms at least partially to an outer shape of the mobile electronic device 50. Still referencing FIG. 14, in one variation, the first case portion 52 includes a wireless power charger/transceiver 72 that is configured to receive electrical power and transmit it to recharge the battery inside the mobile electronic device 50. The charger 72 may be configured to transmit power wirelessly to the battery of the mobile electronic device 50 or, alternatively, the wireless power charger 72 includes a connector 74, as shown in FIG. 14, that is adapted to connect with a corresponding connector of the mobile electronic device 50 and charge the battery directly. The connector 74 extends inwardly from the bottom wall 66 of the first case portion 52. The charger/transceiver 72 is planar and may be attached to the front surface of the back wall 60 as shown or, alternatively, enclosed between the front surface and the back surface of the back wall 60. When a mobile electronic device 50 is inserted into the first case portion 52, the connector 74 connects to the connector on the mobile electronic device 50. In one variation, the wireless power charger/transceiver 72 is omitted from one variation of the first case portion 52. In such a variation, the first case portion 52 is adapted for a mobile electronic device 50 that already includes a built-in wireless charger configured to wirelessly receive power to charge the battery of the mobile electronic device 50. In such a variation, the connector on the mobile electronic device 50 remains exposed and not covered by the bottom wall 66 or by a connector 74.

Figure 7:
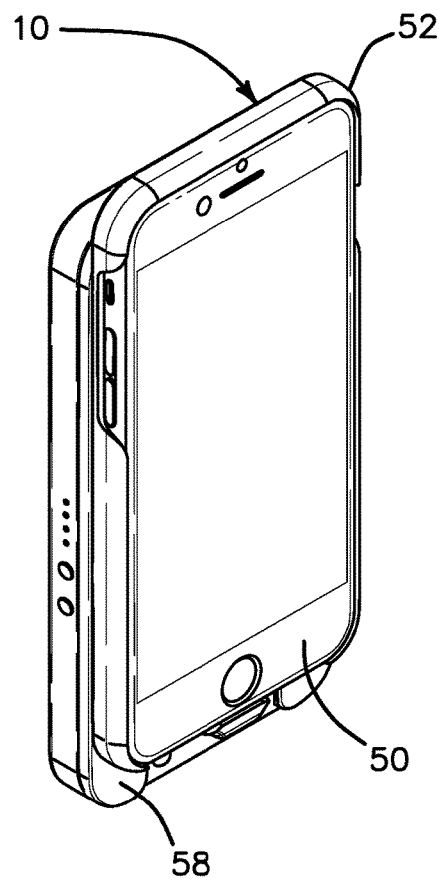
FIG. 7 is a top perspective view of a case connected to a mobile device in sliding attachment to a detachable unit according to the present invention.
Figure 10:
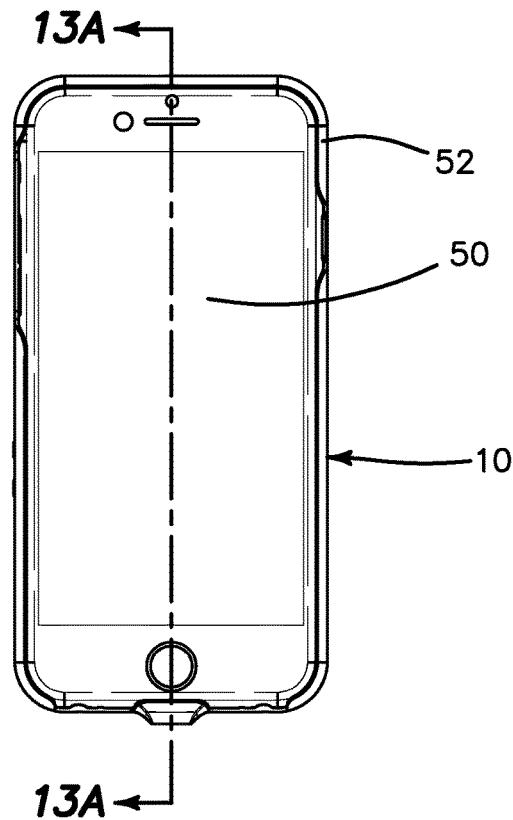
FIG. 10 is a top view of a case connected to a mobile device according to the present invention.
Figure 8:
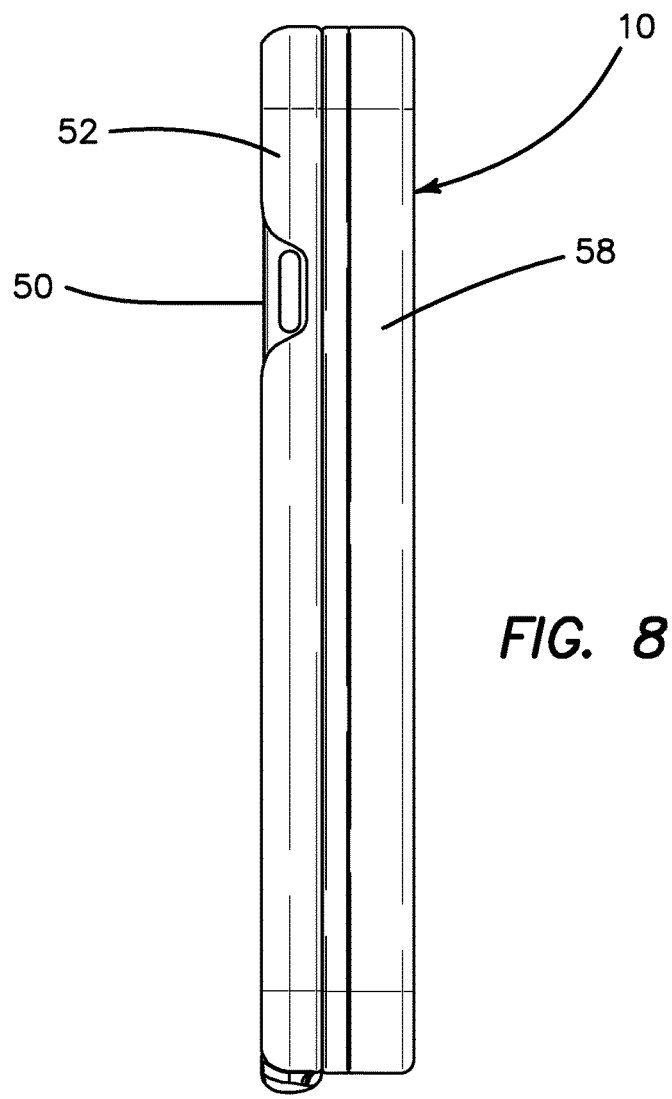
FIG. 8 is a side view of a case connected to a mobile device according to the present invention.
Figure 9:
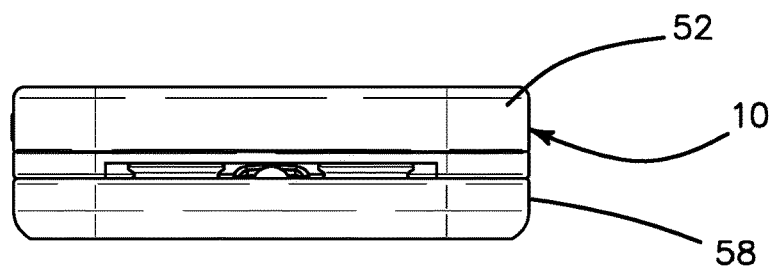
FIG. 9 is an end view of a case connected to a mobile device according to the present invention.
Figure 11:
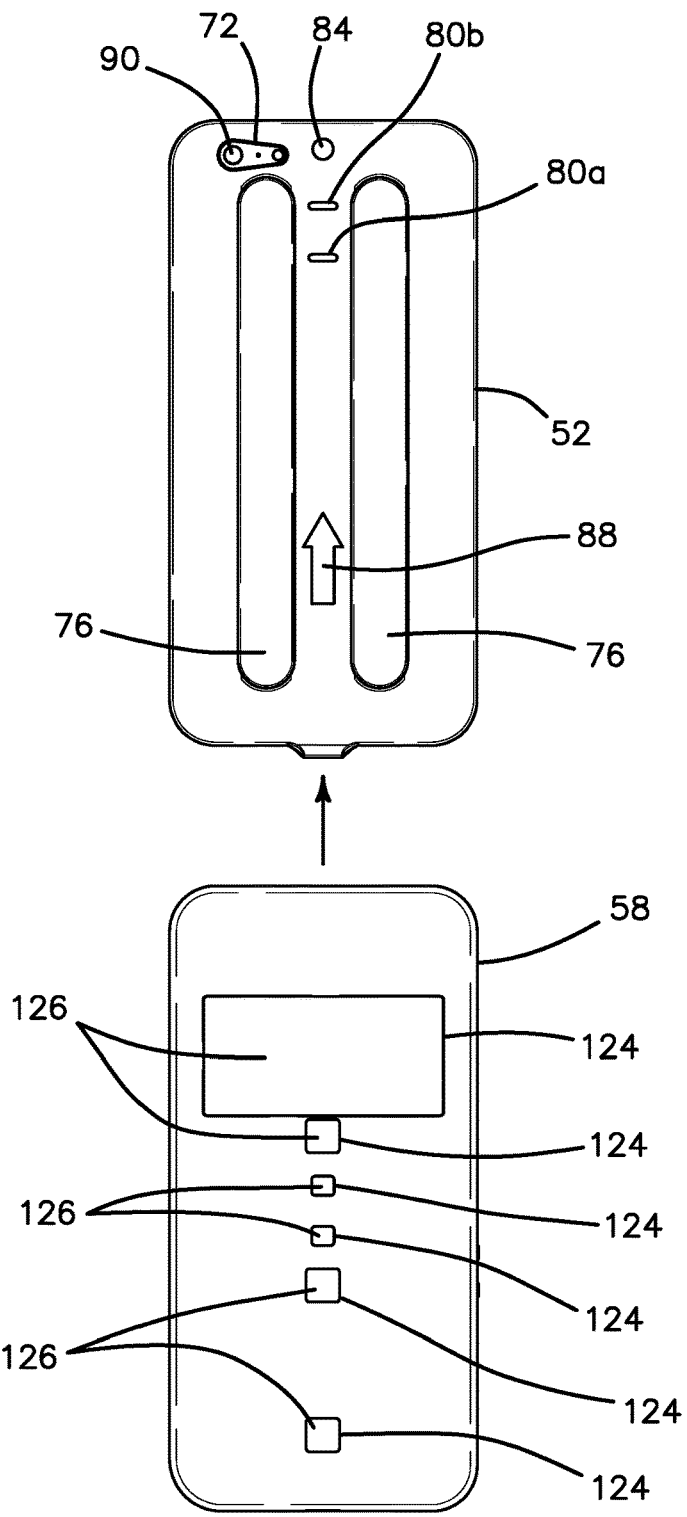
FIG. 11 is a bottom view of a case connected to a mobile device and a detachable unit that is detached according to the present invention.
Figure 12:
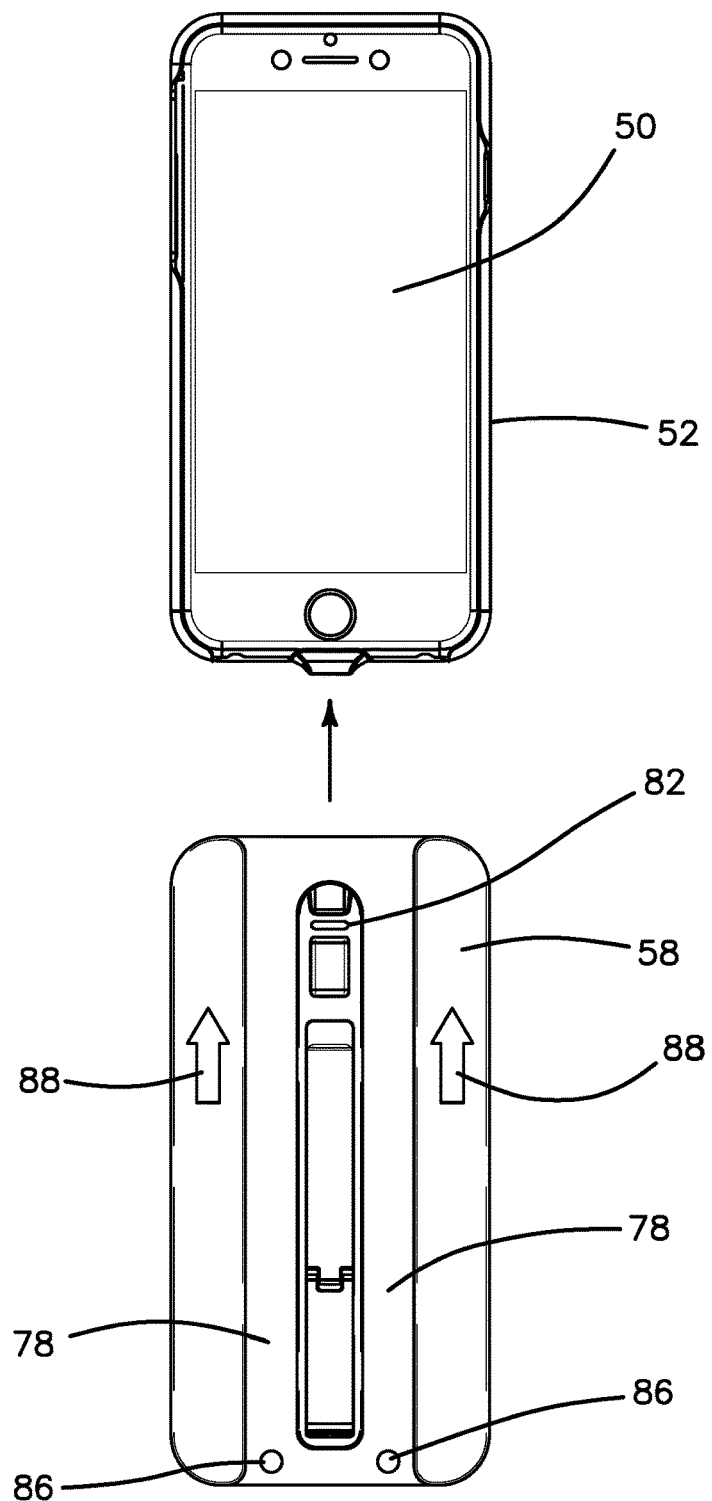
FIG. 12 is a top view of a case connected to a mobile device and a detachable unit that is detached according to the present invention.
Figure 16:
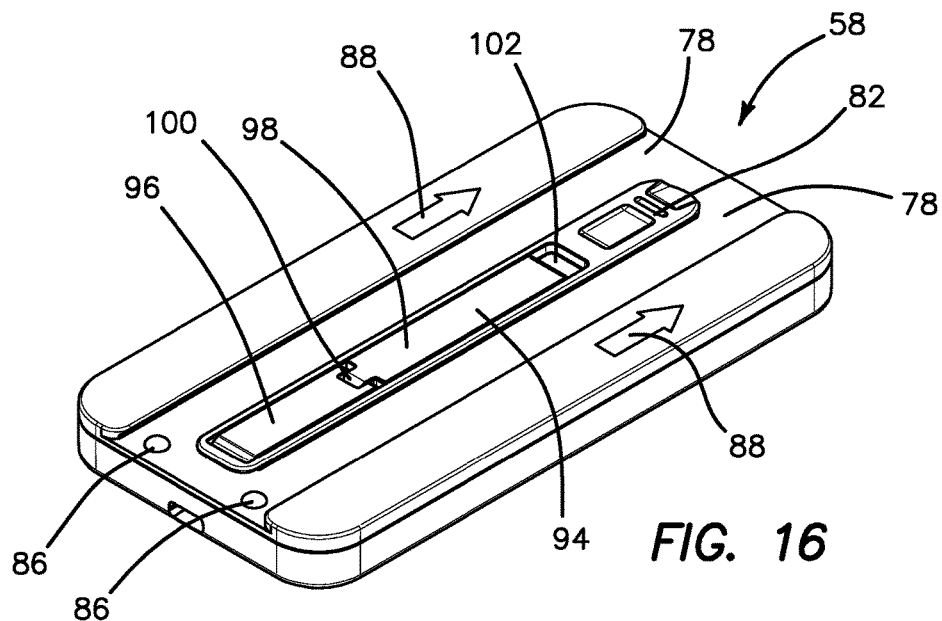
FIG. 16 is a top perspective view of a detachable unit according to the present invention.
Figure 17:
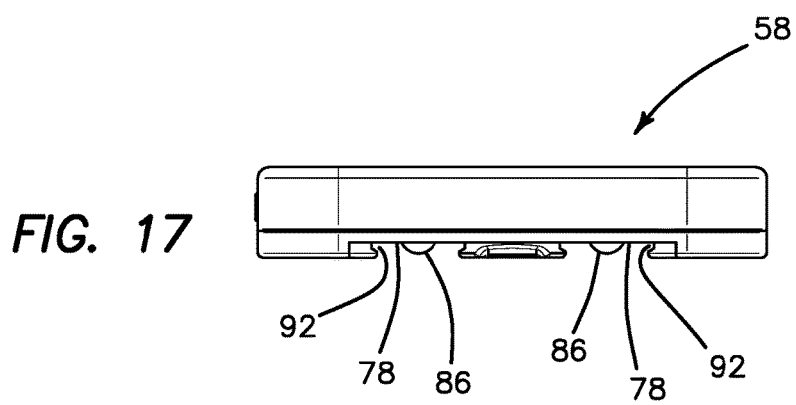
FIG. 17 is an end view of a detachable unit according to the present invention.
Figure 18:
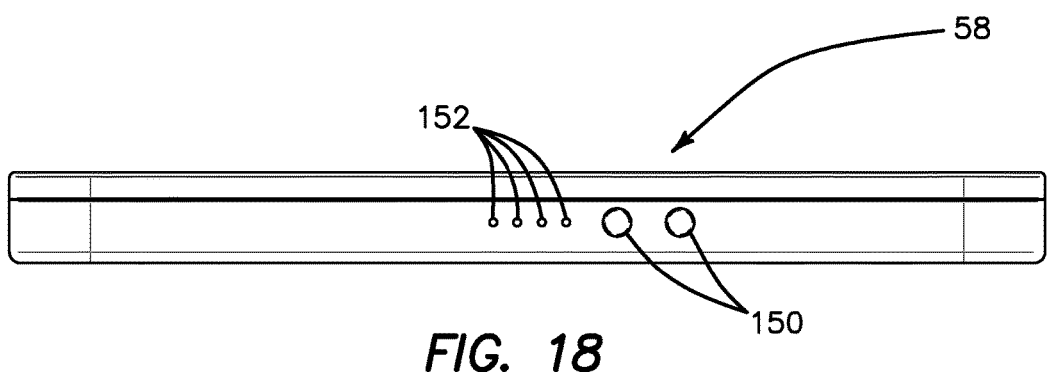
FIG. 18 is a side view of a detachable unit according to the present invention.
Figure 19A:
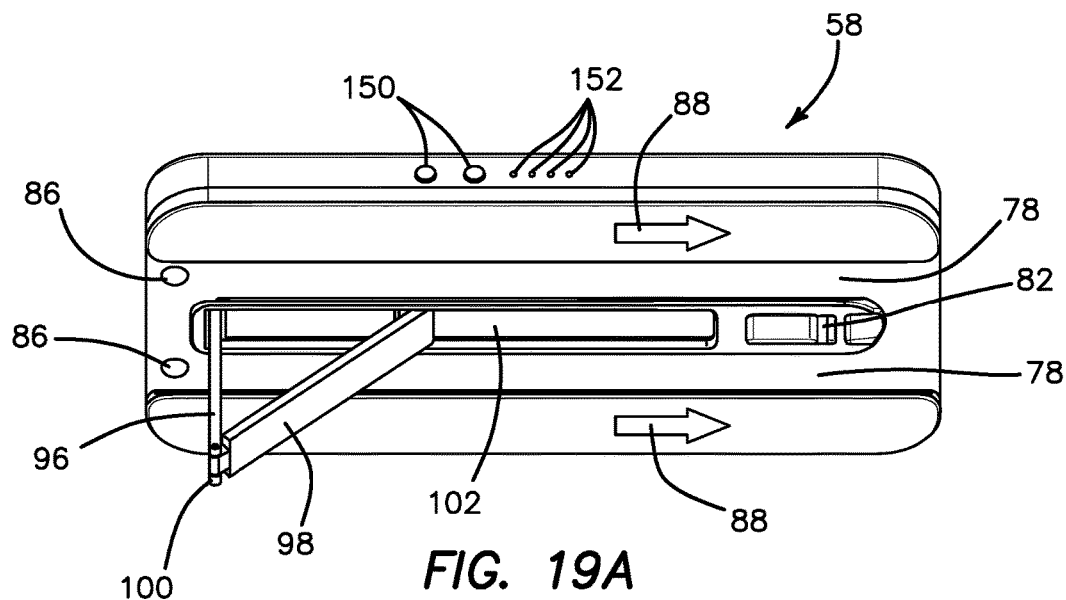
FIG. 19A is a top perspective view of a detachable unit with a retractable stand according to the present invention.
Figure 19G:
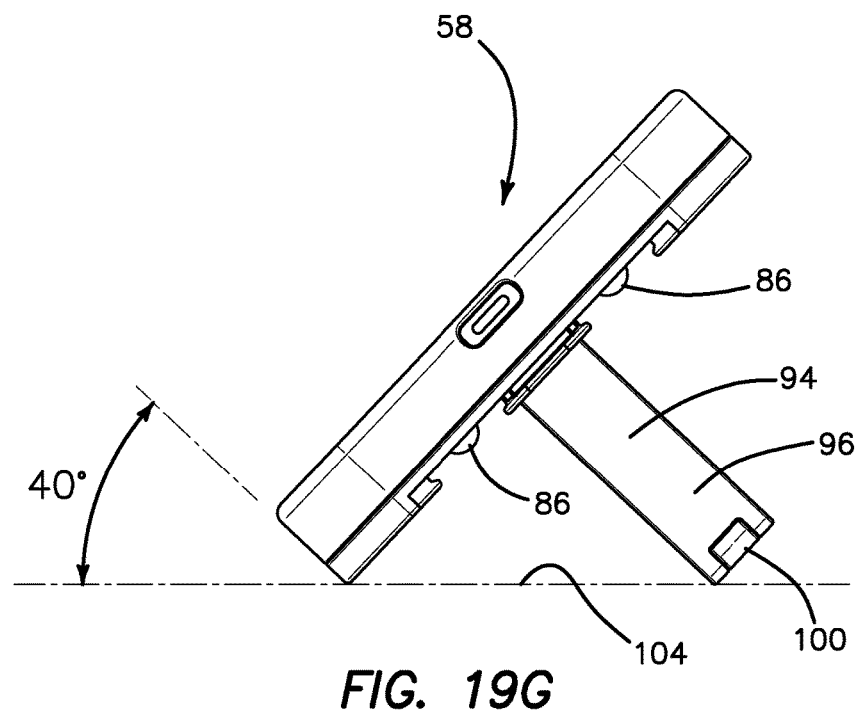
FIG. 19G is a side view of a detachable unit with a retractable stand in an extended position resting with its side against a surface according to the present invention.
Figure 19B:
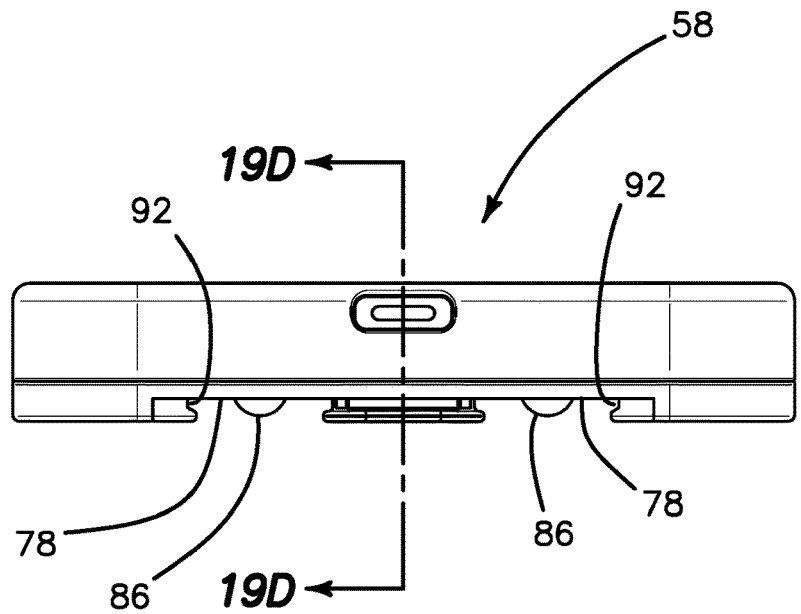
FIG. 19B is an end view of a detachable unit with a retractable stand in a retracted position according to the present invention.
Figure 19C:
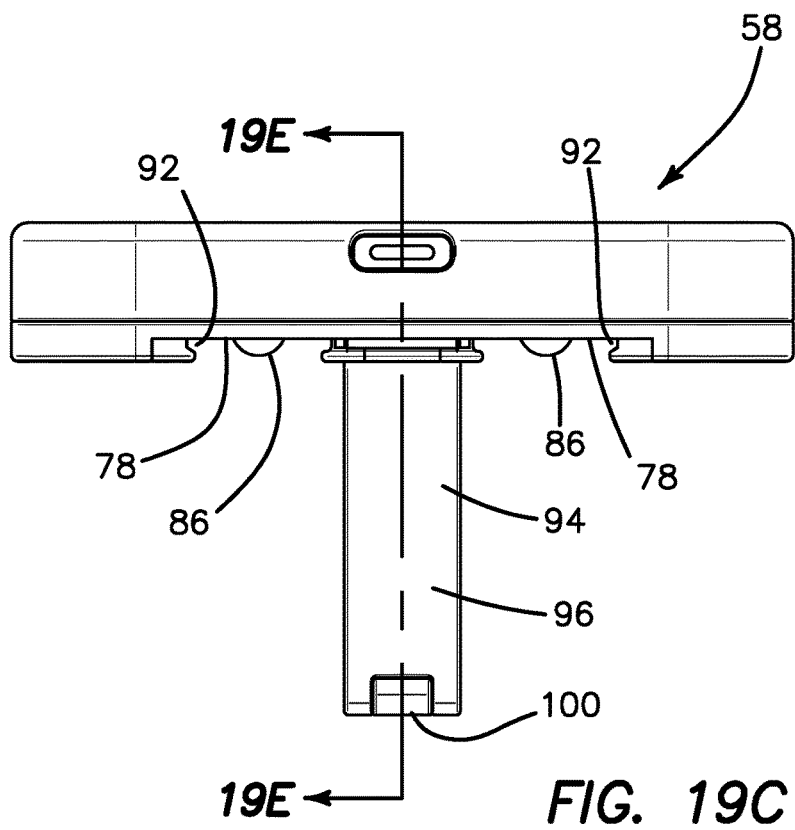
FIG. 19C is a side view of a detachable unit with a retractable stand in an extended position according to the present invention.

Turning now to FIG. 11, the back surface of the back wall 60 of the first case portion 52 will be described in greater detail. The first case portion 52 includes two rails 76 that are raised with respect to the back surface. The rails 76 are parallel and sized and configured to engage corresponding grooves 78 on the second case portion 58 for removable sliding engagement therewith in order to attach and detach the first case portion 52 from the second case portion 58. The grooves 78 on the second case portion 58 are visible in FIGS. 12, 16, 17, 19B and 19C. The back surface of the first case portion 52 further includes two raised male detents 80A, 80B located between the two rails 76 and configured to mate with a female detent 82 located between the two grooves 78 on the second case portion 58. The female detent 82 is shown in FIGS. 12 and 19A. The female detent 82 includes ramped or rounded edges to facilitate engagement and disengagement. The second male detent 80B is located closer to the top of the first case portion 52 than the first male detent 80A. Engagement of the female detent 82 with either one of the male detents 80A, 80B will removably lock the first case portion 52 to the second case portion 58 in a first position and a second position, respectively, along a longitudinal direction of the case. The back surface of the first case portion 52 further includes at least one stop 84 that extends upwardly from the back surface and is located between the two rails 76 near the top end. The second case portion 58 includes two stops 86 in the location of the grooves 78 near the bottom. The stops 86 are visible in FIGS. 12, 16, 17, 19A, 19B and 19C. The stops 84, 86 are configured such that the second case portion 58 can only be inserted from the bottom of the first case portion 52 in order to provide proper orientation and permit engagement of the connector 74 with the connector of the mobile electronic device 50. Directional arrows 88 are also provided on the first and second case portions 52, 58 to indicate to the user the direction of sliding attachment. In use, the user may take note of the arrows 88 and align the top of the second case portion 58 with the bottom of the first case portion 52 as shown in FIGS. 11-12. The rails 76 are aligned with the grooves 78 and the first case portion 52 is moved relative to the second case portion 58 in a sliding motion. The rails 76 may include an undercut that corresponds with an undercut 92 on the grooves 78 to facilitate engagement and prevent separation of the two portions 52, 58 in a tongue-and-groove fashion. The undercut 92 on the groove 78 is visible in FIGS. 17, 19B and 19C. The sliding motion is continued along the rails 76 until the first male detent 80A engages the female detent 82 which arrests the sliding motion in a first position as shown in FIG. 7. In the first position, the top of the second case portion 58 is a separated from the top of the first case portion 52 by a distance. This distance is configured for the particular mobile electronic device 50 such that the aperture of the camera/flash 90 of the mobile electronic device 50 (shown in FIG. 11) is exposed and not blocked by the second case portion 58 permitting the camera/flash 90 to be used without interference from the second case portion 58 covering or entering the picture frame. The first case portion 52 is further movable relative to the second case portion 58 to a second position illustrated in FIGS. 5, 6, 8, 10, 13A and 13B in which the female detent 82 mates with the second male detent 80B. Engagement of the female detent 82 with the second male detent 80B arrests the relative sliding motion in a second position. The second position is noted by the top of the first case portion 52 being aligned/flush with the top of the second case portion 58 such that the perimeters of the first case portion 52 and the second case portion 58 are substantially aligned. The first case portion 52 is movable relative to the second case portion 58 between the first position and the second position. If the user desires to use the camera 90 of the mobile electronic device 50, the first position will uncover the camera lens and aperture. When the camera and lens are not in use, the second position is employed in which the camera lens is covered. The first case portion 52 and the second case portion 58 remain attached together in the first position and second position where the detents 80, 82 are engaged. When the detents 80, 82 are engaged in either the first position or second position, the relative longitudinal translation is restrained by the detents 80, 82 requiring greater force to ramp the male detent 80 from the female detent 82 and overcome the fixed relationship and translate the device to one of the other of the first and second positions or to detach the first case portion 52 from the second case portion 58. With particular reference to FIG. 13B, there is shown a detail of a cross-sectional view illustrating the second male detent 80B engaged with the female detent 82 in a locked second position. Although a sliding snap-fit engagement between the first case portion 52 and the second case portion 58 has been described, the invention is not so limited and any connection means such as magnets and a circular tongue and groove are within the scope of the present invention. All of the features and descriptions of FIGS. 1-4 may be applied to the variations of FIGS. 5-23 and vice-versa.

Figure 19F:
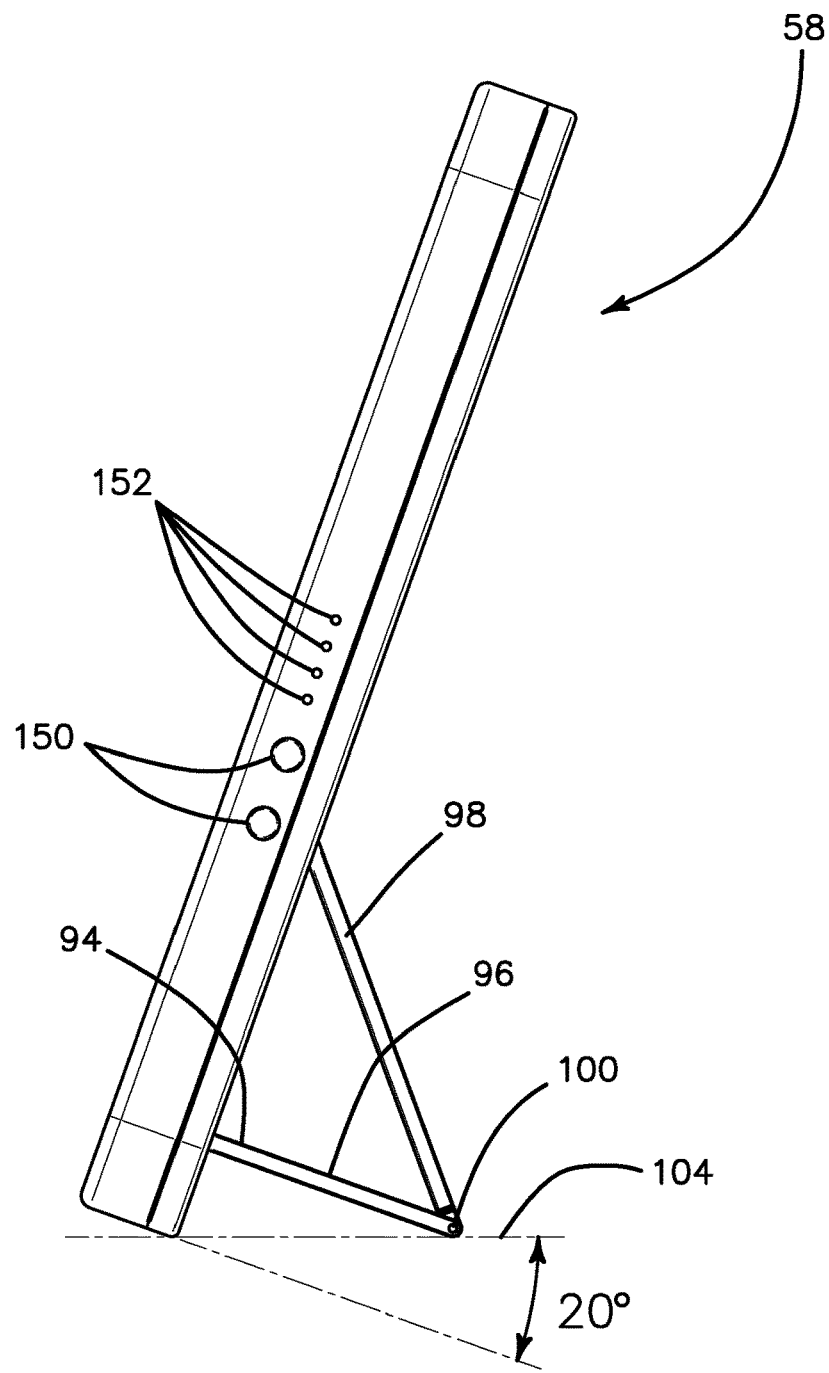
FIG. 19F is a side view of a detachable unit with a retractable stand in an extended position resting with its end against on a surface according to the present invention.

With reference to FIGS. 15 and 19A-19G, the second case portion 58 further includes a retractable stand 94 comprising a first leg 96 connected to second leg 98 via a hinge 100. The outer end of one of the first leg 96 and second leg 98 is fixed and the other ends are movable with respect to the surface of the second case portion 58. For example, as illustrated, one end of the first leg 96 is fixed but permitted to pivot with respect to the second case portion 58 and the other end of the first leg 96 is connected to the second leg 98 via the hinge 100. The opposite end of the second leg 98 is free to translate longitudinally within a channel 102 along the surface between a retracted position illustrated in FIGS. 16-18 and 19B and an extended position of the stand 94 as illustrated in FIGS. 19A, 19C, and 19E-19G. The fixed end of the first leg 96 is proximal to the bottom of the case. The free end of the second leg 98 is retained within the channel 102 such that in the extended position the legs 96, 98 are angled with respect to each other and, in the retracted position, the legs 96, 98 are parallel and lie flush with respect to the front surface of the second case portion 58. The channel 102 is sized and configured to receive the legs 96, 98 in their retracted position such that they do not interfere or enlarge the dimensions of the case. The first leg 96 is shorter than the second leg 98. In use, the second case portion 58 is detached from the first case portion 52 and the second leg 98 is moved with respect to the case to create an angle with the first leg 96 in the extended position. Now the second case portion 58 can be employed as a detached accessory for sanitization or therapy purposes. Advantageously, with the stand in the extended position, the second case portion 58 may be placed on a surface such as a tabletop in one of two upright orientations, a portrait orientation shown in FIG. 19F and a landscape orientation of FIG. 19G. The retractable stand 94 facilitates use of the accessory lights for longer periods of time without requiring the user to hold the second case portion 58. For example, if a therapy light function is selected, the retractable stand 94 is extended and placed on a surface and the therapy lights are turned on. The user may then enjoy hands free use of the accessory. When placed in portrait orientation on a surface 104, the case 58 is angled approximately 20 degrees with respect to the surface 104 as shown in FIG. 19F. When placed in landscape orientation on a surface 104, the case 58 is angled approximately 43 degrees with respect to the surface 104 as shown in FIG.

19G. These orientations conveniently permit the lights housed in the second case portion 58 to be easily directed toward a sanitization target or a part of the user's body which is especially useful in a therapy application of the accessory.

Figure 20:
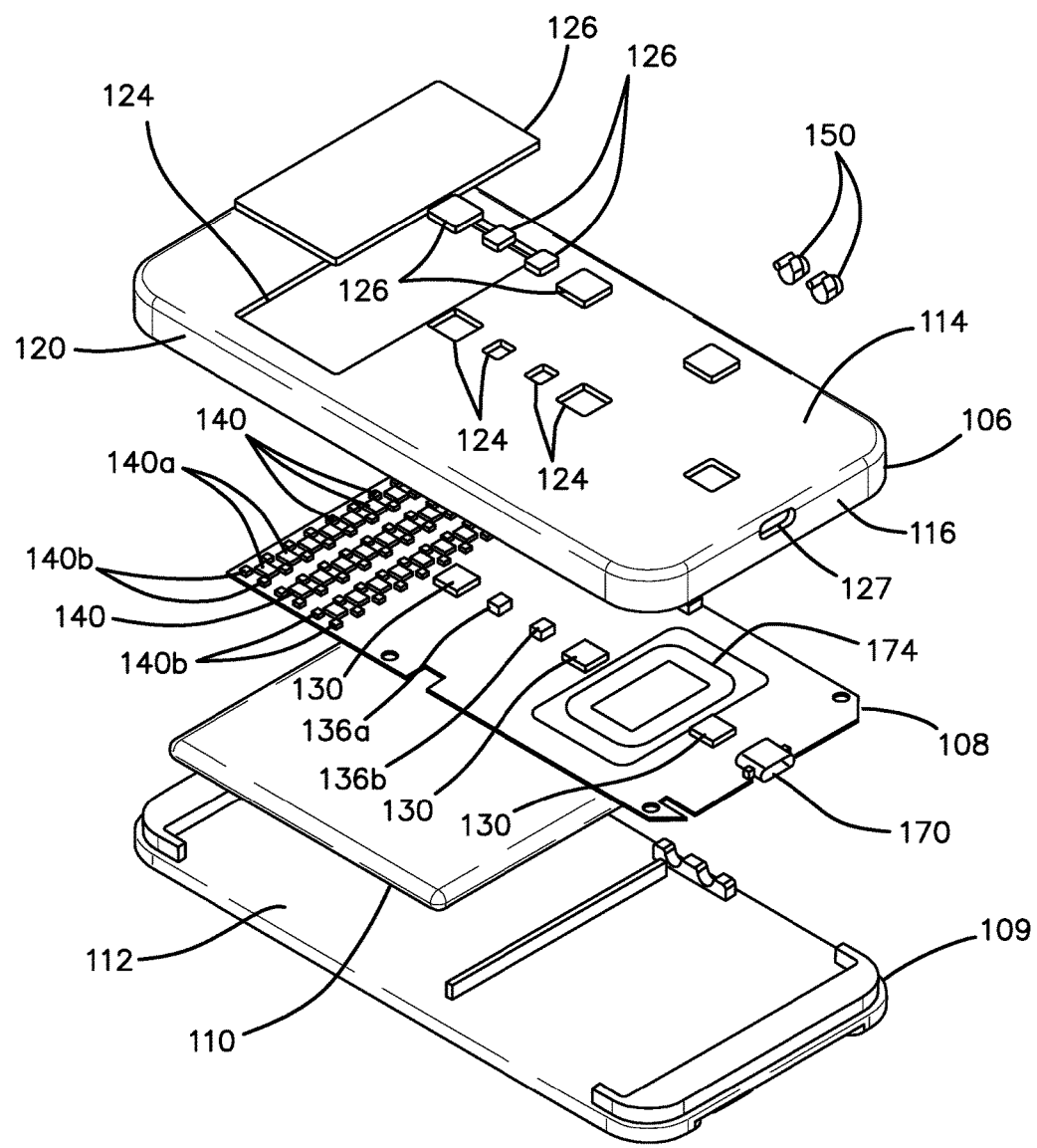
FIG. 20 is an exploded bottom perspective view of a detachable unit according to the present invention.
Figure 21:
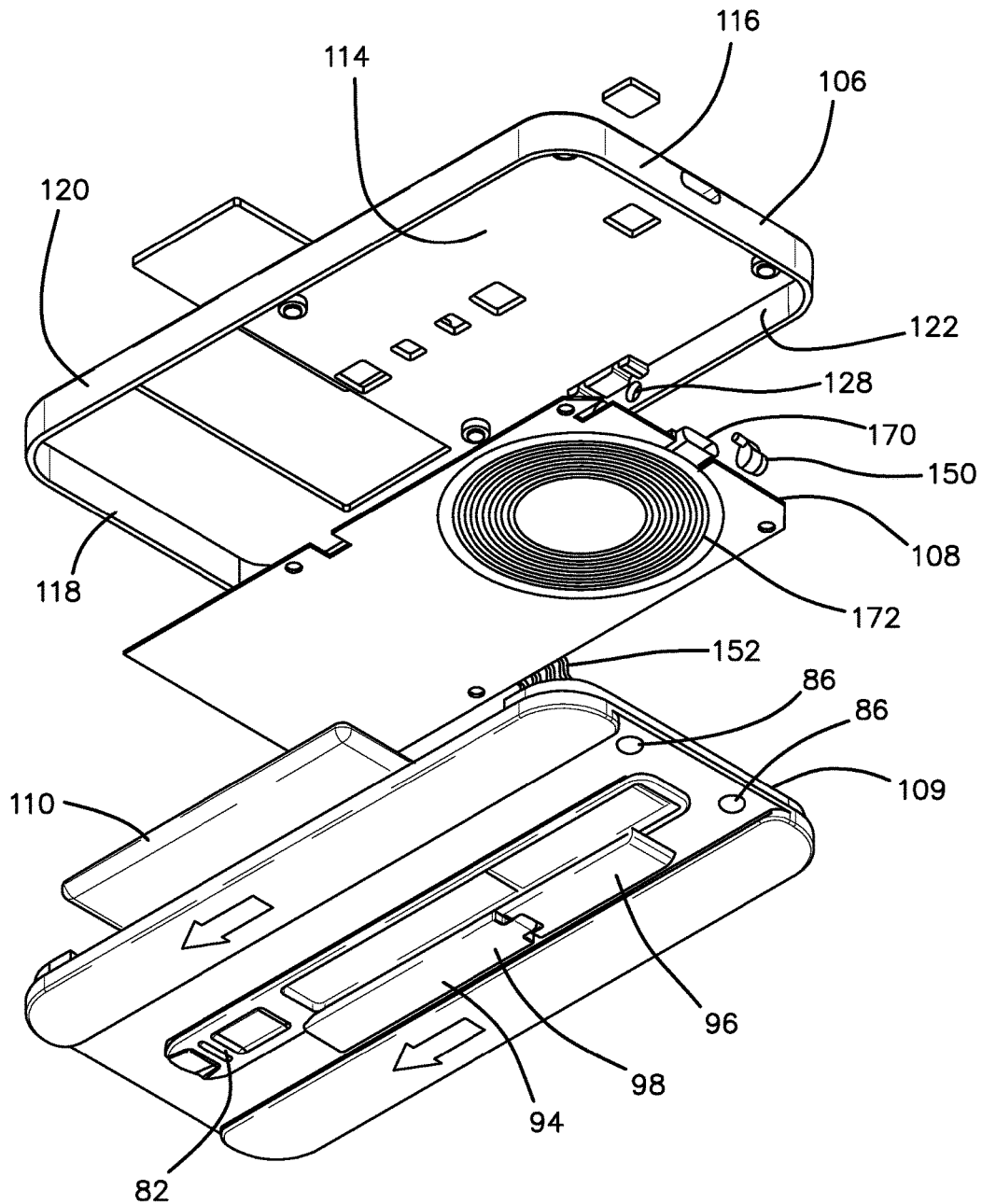
FIG. 21 is an exploded top perspective view of a detachable unit according to the present invention.

Turning now to FIGS. 20-21, the second case portion 58 will now be further described. The second case portion 58 includes a housing 106, circuit board 108, housing cover 109 and a power source such as a battery 110. The housing 106 and housing cover 109 are connected together to define an internal cavity that houses the circuit board 108 and battery 110. The outer front surface of the housing cover 109 is provided with the retractable stand 94 together with mating features for connecting the second case portion 58 to the first case portion 52 as described above. The inner surface of the housing cover 109 is provided with a battery receiving area 112. The inner surface and outer surface of the housing cover 109 define a front wall. The housing 106 includes a back wall 114 interconnected with a bottom wall 116, a top wall 118, a right side wall 120 and a left side wall 122 to define an opening that is closable with the housing cover 109. The back wall 114 includes a plurality of apertures 124 sized, aligned and configured to correspond with various lights/LEDs on the circuit board 108. Each aperture 124 is provided with a transparent window 126 made of glass, plastic or other material affixed to the housing 106 to permit light from the lights/LEDs to pass through. The bottom wall 116 includes an opening 127 for receiving a connector such as for charging the battery 110. The left side wall 122 includes openings 128 for exposing an on/off switch, a mode selector and battery status indicators.

Still referencing FIGS. 21-22 and with further reference to FIG. 22, the circuit board 108 will now be described. The circuit board 108 includes one or more types of lights/LEDs. In one variation, the circuit board 108 includes at least one UV light/LED 130 configured to emit ultraviolet radiation in one or more of the UV wavelength ranges. The variation in the figures includes three UV lights 130. In one variation, the UV light 130 is selected to emit ultraviolet radiation in any one or more wavelength range effective for killing various microbes, and sanitization and disinfection of various surfaces as described above. In another variation, the UV light 130 is selected to emit ultraviolet radiation in the UV-C range. Preferably, the UV light source is a light-emitting diode (LED) and the circuit board 108 includes at least one UV light-emitting diode (LED) which emits UV light. The UV LED 130 is selected to emit radiation in a frequency range effective for killing various microorganisms, preferably in the UV-C range when activated. As the photosensitivity of microorganisms approximately matches the absorption spectrum of DNA, with a peak at about 260 nm, UV LEDs 130 emitting at approximately 250-270 nm are particularly suitable for disinfection and sterilization. UV-A LEDs (having a wavelength of approximately 365 nm) are also known to be effective disinfection and sterilization devices and can also be useful for other applications such as to detect counterfeit currencies. Some examples of semiconductors in UV LEDs include boron nitride, aluminum nitride, aluminum gallium nitride, aluminum gallium indium nitride and diamond. In one variation, the circuit board 108 only includes UV LEDs. In one variation, the circuit includes a variety of UV lights for emitting at the different aforementioned ranges. The UV lights/LEDs 130 are electrically connected to a UV LED controller 132 and in turn to a microcontroller/microprocessor unit 134.

The circuit board 108 may additionally include a white light LED 136A which is connected to white light controller 138 which is in turn connected to the microcontroller unit 134. The white light LED 136A serves as a general purpose illumination such as a flashlight. The circuit board 108 may also include a black light LED 136B for emitting long wave (UV-A) ultraviolet light and not much visible light. The black light LED 136B is useful for authenticating banknotes from counterfeit notes, checking for skin disorders, fungal infections, detecting stains, detecting DNA, detecting contamination and as a bug zapper among other uses. The black light LED 136B is also connected to the same controller 138 as they will not be used simultaneously.

In another variation, the circuit board 108 may additionally or only include color-therapy lights/LEDs 140 connected to a color-therapy controller 142 in turn connected to the microcontroller unit 134. Color-therapy lights/LEDs 140 may include lights/LEDs configured to emit blue light for light therapy purposes such as for treating seasonal affective disorder. In another variation, the circuit board 108 includes a combination of UV LEDs 130 and blue light LEDs. Of course, the circuit board 108 may include only one type of LED or non-LED light or one or more different types of LEDs or non-LEDs on the same circuit board 108 with separate actuation buttons. Some examples of semiconductors in bright blue LEDs are gallium nitride, indium gallium nitride, silicon carbide and silicon. Blue light has a wavelength range of approximately 450-500 nm. Red and green LEDs can be added to blue LEDs to produce the impression of white light. The color-therapy LEDs 140 may include one or more LEDs that emit light in wavelengths ranging from violet (400 nm) to infra-red (1000 nm). FIGS. 20-21 illustrate color-therapy 140 LEDs selected to be blue light LEDs 140A and infra-red LEDs 140B. The infra-red LEDs 140B are connected to an infra-red LED controller 144 and the blue light LEDs 140A are connected to a blue light LED controller 142. Different color-therapy LEDs 140 may be used in conjunction with other color-therapy LEDs 140 such as blue light LEDs 140A and infra-red LEDs 140B and, therefore, each type of color-therapy LED is connected to their respective controller. Various low-level light therapy applications that are well-known in mainstream medicine are listed in Table 1. The present invention may employ one or more LEDs configured to emit any one or more wavelengths for treating the exemplary conditions shown in Table 1 in addition to other LEDs and wavelengths for therapy in the wavelength range of 400-1000 nm.

TABLE 1

| Wavelength (nm) | Color | Condition |
|---|---|---|
| 470 | Blue | acne, hypertrophic scars, keloids |
| 660 | Red | acne, skin rejuvenation, photo protection, herpes lesions, hypertrophic scars, keloids, psoriasis, vitiligo, inflammation, surface lesions, neuralgia, acute and chronic pain, acute and chronic soft tissue injury, tendinitis, bursitis, acute and chronic wounds, deep tissue lesions |
| 694 | Red | hair loss |
| 830 | Near-Infrared | inflammation, neuralgia, acute and chronic pain, acute and chronic soft tissue injury, tendinitis, bursitis, acute and chronic wounds, tendinopathies, arthritis, temporomandibular disorders, orthodontic pain |
| 900 | Near-Infrared | temporomandibular disorders |

The UV LEDs 130 are connected to an UV LED controller 132 and in turn connected to the microcontroller unit 134 and in turn connected to the battery 110, an on/off switch 146, and a mode selector switch 148. In use, the user will depress buttons 150 to activate the power switch 146 to turn the accessory on and then, by repeatedly pressing the mode selector switch 148, cycle through the different modes of operation. By pressing the mode selector switch 148 the microcontroller unit 134 activates the corresponding operation such as indicating battery charge status, turning wireless charging of the mobile electronic device 50 on and off, activating black/white light LEDs, and activating UV LEDs. Battery charging status LEDs 152 are provided to indicate how much power is available. These controls conveniently permit the user to use the accessory quickly and independently of the mobile electronic device 50 including while the second case portion 58 is detached from the first case portion 52.

Figure 23:
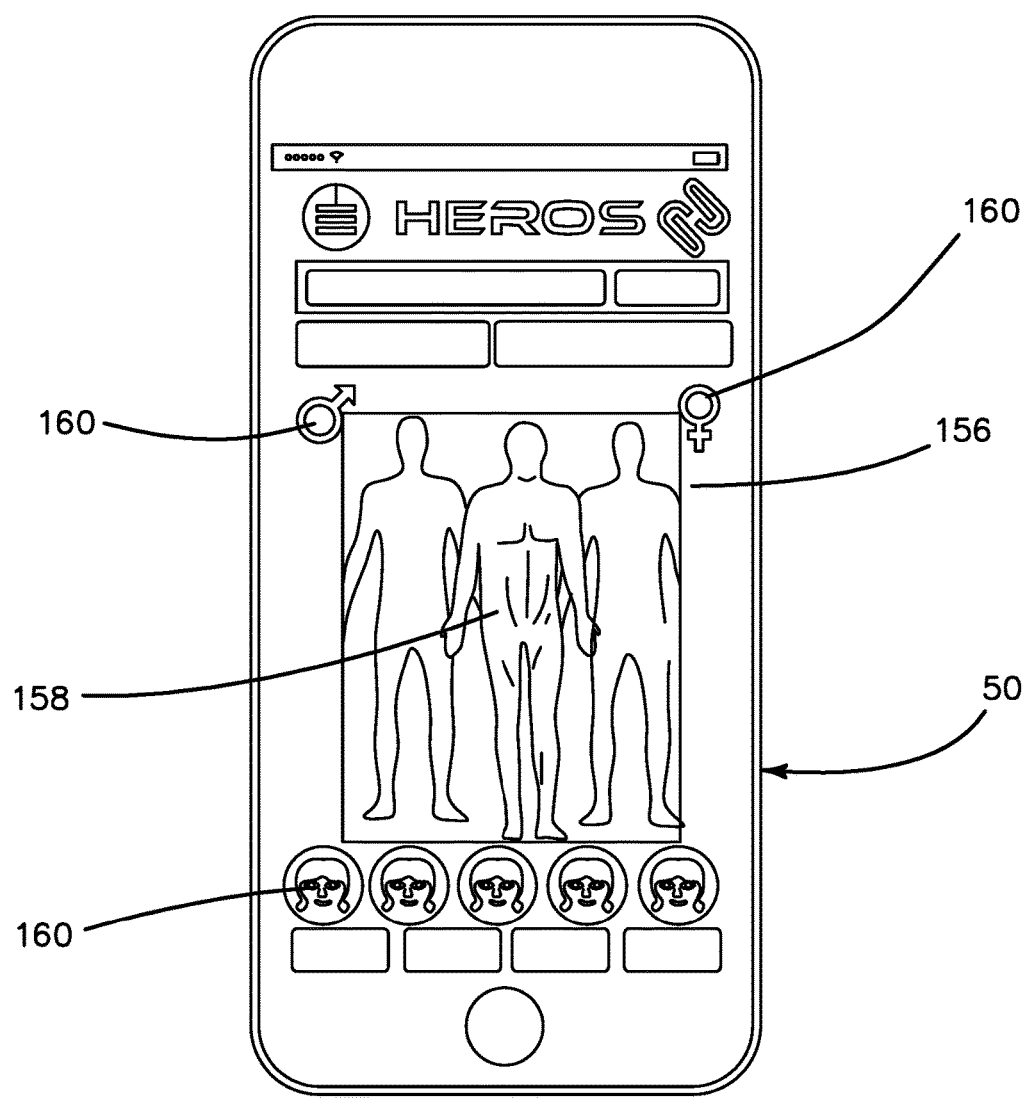
FIG. 23 is a depiction of a graphic user interface appearing on a mobile device according to the present invention.

The color-therapy LEDs 140 are connected to their one or more respective color-therapy LED controllers 142, 144 as needed. The color-therapy LED controllers 142 are in turn connected to the microcontroller unit 134 as well as to a BLUETOOTH low-energy, short-range wireless receiver 154 for transmitting data over short distances between the circuit board 108 of the second case portion 58 and the mobile electronic device 50. On the mobile electronic device 50, a software application is installed to provide the user with a graphical user interface such as that illustrated in FIG. 23 for the control of the color-therapy LEDs 140. The data input from the user is transmitted from the mobile electronic device 50 to the wireless receiver 154 and to the controllers 134, 142 etc. The software application installed on the mobile electronic device 50 allows the user to interface via the wireless connection between the mobile electronic device 50 and the case. The software application will include pre-programmed settings for the activation, intensity, duration, etc. of the various color-therapy LED wavelengths and frequencies of light that affect different tissues of the body including Nogier frequencies for different conditions/organs/systems that the user wishes to treat such as but not limited to inflammation, traumatic injuries, muscle healing, sports recovery, sleep aid, etc. The software application on the graphical user interface will guide the user where to apply and direct the light from the light therapy LEDs using input from the user via a touch screen or text input of the specific condition being treated. An illustration of the body's anatomy 158 after selecting the light-receiver's sex 160 may be displayed as shown in FIG. 23 highlighting a target organ, energy meridian, acupuncture meridian, chakra guides and the like given the selected treatment desired. The application will guide the user where to apply the light therapy using the illustration 158 of the body and its different systems. The software application will also adjust for the skin color of the user after receiving input on the skin color selector 160. The application will also include pre-programmed settings for sanitizing purposes for different types of surfaces and adjusting the frequency and duration to accomplish the greatest effect. As such, the UV LEDs 130 may also employ the BLUETOOTH receiver to receive data from the application on the mobile electronic device 50 for custom and target-specific control of the UV LEDs 130 and/or therapy and/or other LEDs 140. In one variation, the software application on the mobile electronic device 50 is configured to control all of the LEDs and, therefore, the second case portion 58 does not include one or more of the on/off switch 146, mode selector switch 148, buttons 150 and battery status LEDs 152.

Figure 22:
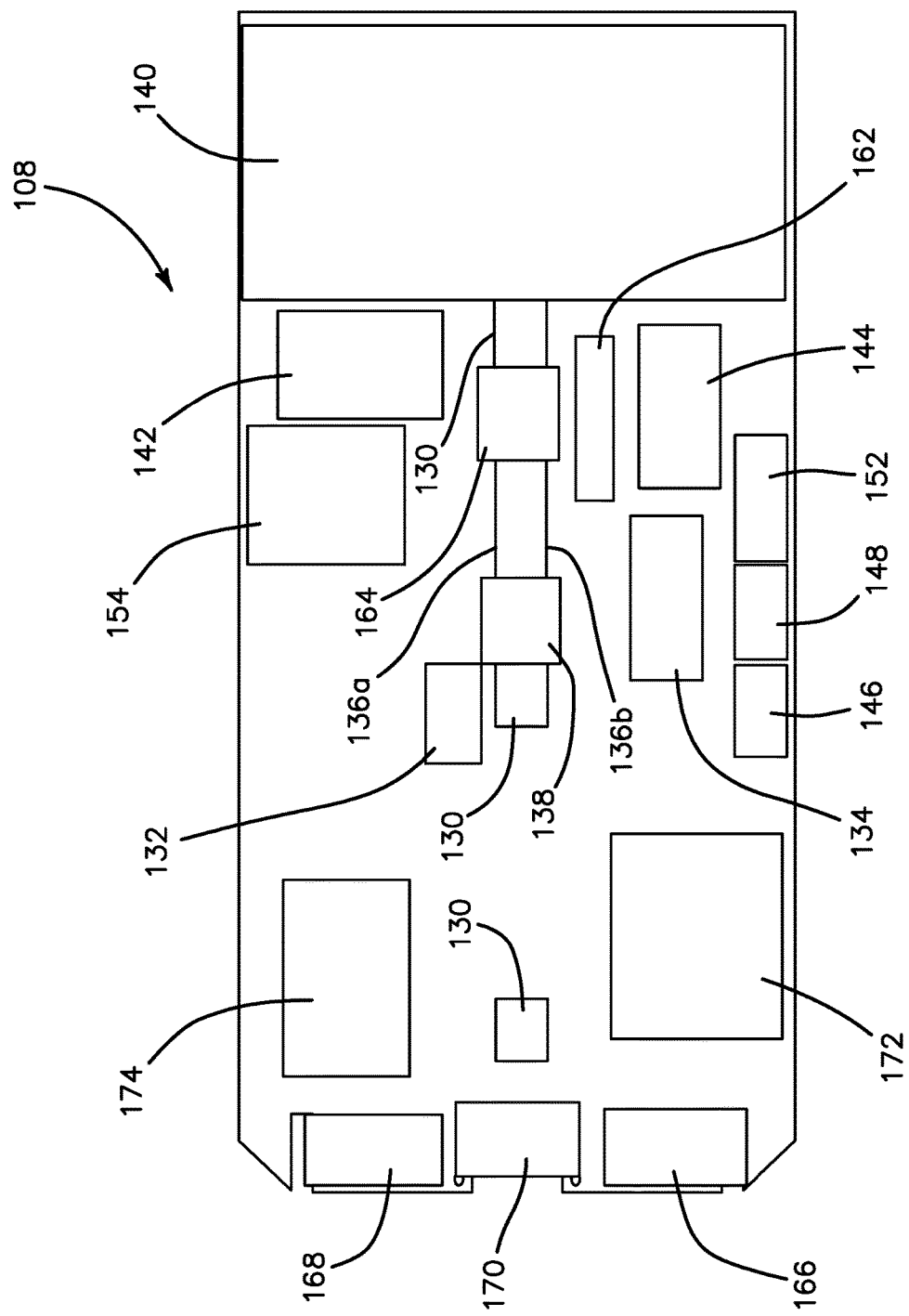
FIG. 22 is a schematic of a circuit board of a detachable unit according to the present invention.

Still referencing FIGS. 20-22, certain safety features are included on the circuit board 108 and connected to the microcontroller unit 134. In one variation, an accelerometer 162 is provided. The accelerometer 162 provides orientation information of the device such as whether it is facing downwardly or upwardly. The safety feature employs the data from the accelerometer 162 to activate and/or deactivate the particular light/LED. For example, if the second case portion 58 is facing downward, the microcontroller unit 134 will receive such data from the accelerometer 162 and will activate the selected light/LED or keep a light/LED activated. If the second case portion 58 is facing upwardly or other specified angle, the programming will, for example, deactivate the selected light/LED so as to not shine the device into a person's face. Alternatively, or in conjunction with the accelerometer 162, a proximity sensor 164 is provided on the circuit board 108 to serve an additional safety function. For example, if the proximity sensor 164 detects that the light-emitting surface of the device is not detecting a surface in close proximity or that the device is far from any surface, it will not turn on any LEDs or will turn off the LEDs so as to not only save battery power when the effective distance is too far, but also, to avoid unwanted light being directed into a person's eyes.

Furthermore, a BLUETOOTH wireless communication programming port 166 is provided and connected to the wireless receiver 154 for establishing a connection with the mobile electronic device 50. Also, a microcontroller programming port 168 is provided on the circuit board 108 to enable the microcontroller unit 134 to be programmed or data from its memory to be downloaded.

In order to charge the battery 110 of the accessory, a connector 170, such as USB Type-C connector, is further included on the circuit board 108 and connected to the battery 110. The battery 110 is connected to the electronic circuitry of the circuit board 108. In one variation, the connector 170 is used for connecting with a wire to a power source for directly charging the battery 110. The battery 110 may also be configured to be charged wirelessly and as such is provided with a wireless receiver 174 that is configured to receive power wirelessly from an external power transmitter. The battery 110 of the accessory may also be used for charging the battery of the mobile communication device 50 to which it is attached. In order to charge the battery of the mobile electronic device 50, the circuit board 108 is further provided with a wireless transmitter 172 that is located proximate to the battery of the mobile electronic device 50 when the first case portion 52 and the second case portion 58 are connected. The wireless transmitter 172 includes a transmit circuit configured to wirelessly retransmit power from the battery 110 to the wireless power charger 72 containing a wireless power receiver located in the first case portion 52 which is connected directly to the battery inside the mobile electronic device 50 via the connector 74. If the mobile electronic device 50 already has wireless charging capability, the wireless charger 72 is omitted from the first case portion 52 and the wireless transmitter 172 can transmit power to a wireless power receiver located directly inside the mobile electronic device 50 where it is can then charge the battery of the mobile electronic device 50.

LEDs are advantageously small and make them suitable for portable applications such as the accessory of the present invention where compactness is important. LEDs also provide a very high brightness with high-efficiency. The LEDs can have any shape and can be arranged in any manner. For example, the LEDs can be arranged in a linear fashion along one side of the circuit 108 or in a rectangular or circular pattern to allow for different surface coverage configurations. In one variation, the LEDs are located anywhere on the outer surface of the second case portion 58. Preferably, the LEDs are located on the base backside such that the LEDs are located opposite from the visual display of the mobile electronic device 58. Thereby, the user may view the visual display of the mobile electronic device 58 to monitor the activation and duration of the LEDs while directing the light away from the user. The UV LEDs 130 are configured to disinfect while the blue light LEDs 140 are configured for light therapy. The power output of the LEDs will vary depending on the desired irradiance intensity allowing for a wide range of effectiveness. Of course, the accessory includes any combination of one or more lights/LEDs described in this specification.

According to variations of the present invention, one or more LEDs can emit multiple wavelengths ranging from about 100 to about 1000 nm. By way of example only, a single LED can be used in which the LED emits radiation primarily at two wavelengths. Alternatively, variations of the present invention can include multiple LEDs wherein each LED emits radiation at different and distinct wavelengths to more completely irradiate a surface in a region ranging from about 210 to about 300 nm. In other embodiments, the sanitization device can include multiple LEDs wherein each LED, or group of LEDs which can be configured into an array, emits radiation at a single and different wavelength.

It is understood that various modifications may be made to the embodiments and variations disclosed herein. Therefore, the above description should not be construed as limiting, but merely as exemplifications of preferred embodiments. Those skilled in the art will envision other modifications within the scope and spirit of the present disclosure.

I claim:

1. A portable light treatment device for use with a mobile electronic device comprising:
    a casing configured to be removably connectable to a mobile electronic device;
    at least one light source connected to the casing and configured to emit electromagnetic radiation in a direction away from the casing;
    a power source connected to the casing and configured to power the at least one light source;
    at least one controller connected to the at least one light source and configured to receive input from the mobile electronic device;
    a software application installed on the mobile electronic device and configured to receive input from a user via a graphical user interface for the control of the at least one light source;
    wherein the at least one controller is wirelessly connected to the mobile electronic device; and
    wherein the software application includes pre-programmed settings for intensity, duration and frequency of wavelengths of light that have a therapeutic effect on various medical conditions affecting different tissues or surfaces of the human body.

2. A portable light treatment device for use with a mobile electronic device comprising:
    a casing configured to be removably connectable to a mobile electronic device;
    at least one light source connected to the casing and configured to emit electromagnetic radiation in a direction away from the casing;
    a power source connected to the casing and configured to power the at least one light source;
    at least one controller connected to the at least one light source and configured to receive input from the mobile electronic device;
    a software application installed on the mobile electronic device and configured to receive input from a user via a graphical user interface for the control of the at least one light source;
    wherein the at least one controller is wirelessly connected to the mobile electronic device; and
    wherein the software application includes pre-programmed settings configured for the activation, intensity or duration of the at least one light source for different tissues or surfaces.

3. The device of claim 2 wherein the at least one light source emits light in the UV spectrum of electromagnetic radiation.

4. The device of claim 2 wherein the at least one light source emits light in the color spectrum of electromagnetic radiation.

5. A portable light treatment device for use with a mobile electronic device comprising:
    a casing configured to be removably connectable to a mobile electronic device;
    at least one light source connected to the casing and configured to emit electromagnetic radiation in a direction away from the casing;
    a power source connected to the casing and configured to power the at least one light source;
    at least one controller connected to the at least one light source and configured to receive input from the mobile electronic device;
    a software application installed on the mobile electronic device and configured to receive input from a user via a graphical user interface for the control of the at least one light source;
    wherein the at least one controller is wirelessly connected to the mobile electronic device;
    wherein the software application includes pre-programmed settings for the activation, intensity or duration of wavelengths and frequencies of light to treat muscle healing, improve sports recovery or sleep.

6. The device of claim 5 wherein the software application provides information to guide the user where to apply and direct the light from the at least one light source.

7. A portable light treatment device for use with a mobile electronic device comprising:
    a casing configured to be removably connectable to a mobile electronic device;
    at least one light source connected to the casing and configured to emit electromagnetic radiation in a direction away from the casing;
    a power source connected to the casing and configured to power the at least one light source;
    at least one controller connected to the at least one light source and configured to receive input from the mobile electronic device;
    a software application installed on the mobile electronic device and configured to receive input from a user via a graphical user interface for the control of the at least one light source;
    wherein the at least one controller is wirelessly connected to the mobile electronic device; and
    wherein the input is of a specific medical condition being treated with the at least one light source via a touch screen on the mobile electronic device or via text; and
wherein the input is received by the software application via the graphical user interface.

8. A portable light treatment device for use with a mobile electronic device comprising:
a casing configured to be removably connectable to a mobile electronic device;
at least one light source connected to the casing and configured to emit electromagnetic radiation in a direction away from the casing;
a power source connected to the casing and configured to power the at least one light source;
at least one controller connected to the at least one light source and configured to receive input from the mobile electronic device;
a software application installed on the mobile electronic device and configured to receive input from a user via a graphical user interface for the control of the at least one light source;
wherein the at least one controller is wirelessly connected to the mobile electronic device; and
wherein the graphical user interface displays a pre-programmed illustration of a human body, organ, energy meridian, acupuncture meridian, or chakra.

9. A portable light treatment device for use with a mobile electronic device comprising:
a casing configured to be removably connectable to a mobile electronic device;
at least one light source connected to the casing and configured to emit electromagnetic radiation in a direction away from the casing;
a power source connected to the casing and configured to power the at least one light source;
at least one controller connected to the at least one light source and configured to receive input from the mobile electronic device;
a software application installed on the mobile electronic device and configured to receive input from a user via a graphical user interface for the control of the at least one light source;
wherein the at least one controller is wirelessly connected to the mobile electronic device; and
wherein the software application is configured to provide instructions to guide the user as to where to apply the light for therapeutic or sanitizing effect using a pre-programmed illustration displayed on the graphical user interface.

10. The device of claim 2 wherein the software application is configured to adjust the intensity and duration of the light source for the skin color of the user.

11. The device of claim 3 wherein the software application includes pre-programmed settings for sanitizing purposes.

12. The device of claim 11 whereupon receiving input at the graphical user interface as to the type of surface the software application controls at least one controller to adjust the frequency and duration of the emitted light.

13. A method comprising the steps of:
connecting a case to a mobile electronic device; the mobile electronic device having a graphical user interface and the case including at least one light source configured to emit electromagnetic radiation in a direction away from the case;
selecting a pre-programmed therapeutic treatment protocol displayed on the graphical user interface;
displaying guidance to the user on the graphical user interface as to where to direct the electromagnetic radiation emitted from the at least one light source; and
activating the at least one light source to emit electromagnetic radiation.

14. The method of claim 13 further including the step of selecting a sanitization protocol.

15. The method of claim 13 wherein the step of displaying guidance includes displaying an illustration of anatomy, a target organ, energy meridian, acupuncture meridian or chakra.

16. The method of claim 13 further including the step of adjusting the intensity or duration of the electromagnetic radiation emitted from the at least one light source based on skin color.

17. The method of claim 14 wherein selecting a sanitization protocol by a user includes the step of activating a light source configured to emit UV light.

18. The method of claim 13 further including the step of adjusting the frequency or wavelength of the electromagnetic radiation emitted from the at least one light source applied to different tissues or surfaces of the human body to attain a therapeutic effect.

19. The method of claim 13 wherein the step of activating the at least one light source includes automatically selecting the frequency and duration of electromagnetic radiation.

* * * * *